United States Patent
Achour et al.

(10) Patent No.: US 9,623,012 B2
(45) Date of Patent: *Apr. 18, 2017

(54) FORMULATION COMPRISING BENZOTHIAZOLONE COMPOUND

(71) Applicant: Novartis AG, Basel (CH)

(72) Inventors: Miloud Achour, Basel (CH); Robin Alec Fairhurst, Basel (CH); Arnaud Grandeury, Basel (CH); Shinji Hatakeyama, Basel (CH); Magdalena Koziczak-Holbro, Basel (CH); Nicola Tufilli, Basel (CH); Thomas Ullrich, Basel (CH)

(73) Assignee: NOVARTIS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/770,819

(22) PCT Filed: Feb. 26, 2014

(86) PCT No.: PCT/IB2014/059270
§ 371 (c)(1),
(2) Date: Aug. 26, 2015

(87) PCT Pub. No.: WO2014/132205
PCT Pub. Date: Sep. 4, 2014

(65) Prior Publication Data
US 2016/0000761 A1  Jan. 7, 2016

Related U.S. Application Data

(60) Provisional application No. 61/770,584, filed on Feb. 28, 2013.

(51) Int. Cl.
*A61K 31/428* (2006.01)
*A61K 31/19* (2006.01)
*A61K 9/00* (2006.01)
*A61K 9/20* (2006.01)
*A61K 9/48* (2006.01)

(52) U.S. Cl.
CPC .......... *A61K 31/428* (2013.01); *A61K 9/0053* (2013.01); *A61K 9/2018* (2013.01); *A61K 9/2054* (2013.01); *A61K 9/485* (2013.01); *A61K 9/4858* (2013.01); *A61K 9/4866* (2013.01); *A61K 31/19* (2013.01)

(58) Field of Classification Search
CPC .... A61K 31/19; A61K 31/428; A61K 9/0053; A61K 9/2018; A61K 9/2054; A61K 9/485; A61K 9/4858; A61K 9/4866
See application file for complete search history.

(56) References Cited

U.S. PATENT DOCUMENTS

2013/0245080 A1* 9/2013 Cao ................ C07D 277/68
514/367

FOREIGN PATENT DOCUMENTS

WO   2006/056471 A1   6/2006
WO   2013/035047 A1   3/2013

OTHER PUBLICATIONS

Rudnic (Oral solid dosage forms, chapter 92, Remington : The science and practice of pharmacy, 1995, pp. 1615-1648).*

* cited by examiner

*Primary Examiner* — Savitha Rao
(74) *Attorney, Agent, or Firm* — John B. Alexander

(57) ABSTRACT

The present invention relates to a pharmaceutical composition in solid oral dosage form comprising (R)-7-(2-(1-(4-butoxyphenyl)-2-methylpropan-2-ylamino)-1-hydroxyethyl)-5-hydroxybenzo[d]thiazol-2(3H)-one acetate salt.

13 Claims, 9 Drawing Sheets

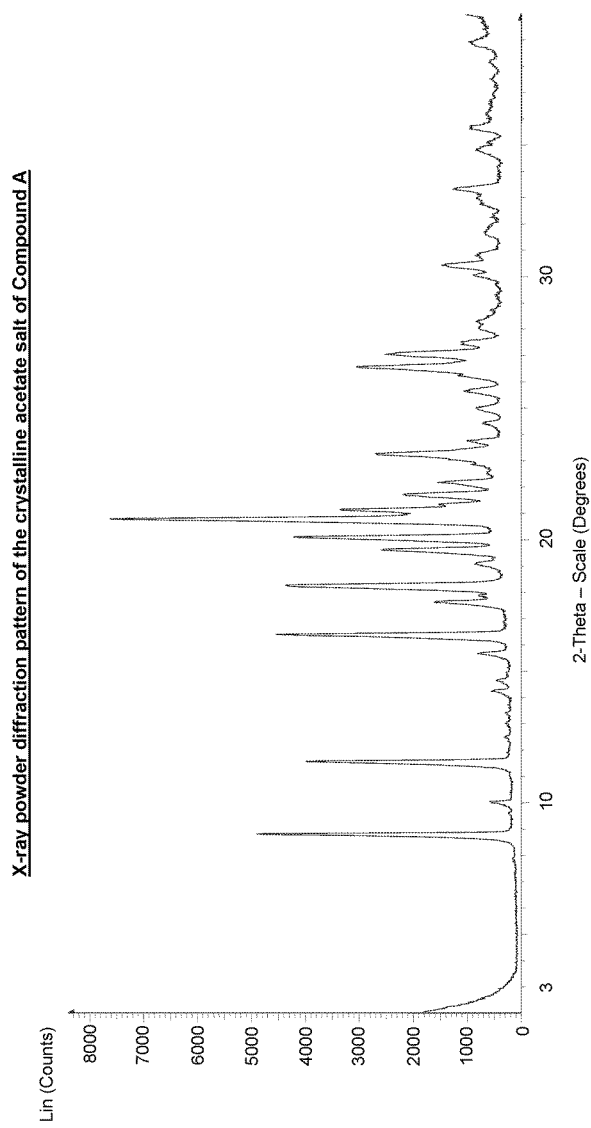

FORMULATION COMPRISING BENZOTHIAZOLONE COMPOUND

This application is a U.S. National Phase filing of International Application No. PCT/IB2014/059270 filed 26 Feb. 2014, which claims priority to U.S. Application No. 61/770,584 filed 28 Feb. 2013, the contents of which are incorporated herein by reference in their entirety.

FIELD OF THE INVENTION

The present invention relates to novel pharmaceutical compositions comprising (R)-7-(2-(1-(4-butoxyphenyl)-2-methylpropan-2-ylamino)-1-hydroxyethyl)-5-hydroxybenzo[d]thiazol-2(3H)-one, to methods of manufacturing such compositions and to the use thereof in the treatment or prevention of diseases such as muscular dystrophy, disuse-related atrophy, cachexia or sarcopenia.

BACKGROUND OF THE INVENTION

Benzothiazolone compounds which are beta-2-adrenoceptor agonists are described in WO2004/16601 and WO2006/056471. WO2005/110990 also describes benzo-condensed heterocycles as beta-2 agonists.

While beta-2 agonists have long been known for their bronchodilating properties, they are also known for their capability to produce skeletal muscle hypertrophy.

Numerous studies have focused on therapeutic applications of the anabolic properties of beta-2 agonists for ameliorating muscle wasting and improving muscle function. However, this class of compounds has also been associated with undesirable side-effects, including increased risk of adverse cardiovascular-related events. Thus, the use of beta-2 agonists in muscle wasting diseases has hitherto been limited by cardiac hypertrophy and potentially deleterious effects on cardiovascular function.

There is a need to provide new beta-2 agonists that are good drug candidates. In particular, a new beta-2 agonist should bind potently to the beta-2 adrenoceptor whilst showing little affinity for other receptors, such as e.g. the beta-1 adrenoceptor, the alpha-1A adrenoceptor, or the $5HT_{2C}$ receptor, and show functional activity as an agonist. It should be metabolically stable and possess favourable pharmacokinetic properties. It should be non-toxic and demonstrate few side-effects, in particular fewer cardiac side-effects than known marketed beta-2 agonists, such as e.g. formoterol. Furthermore, the ideal drug candidate will exist in a physical form that is stable, non-hygroscopic and easily formulated.

SUMMARY OF THE INVENTION

There is therefore a need to provide a compound having at least some of the properties described above wherein the compound is in a physical form which may improve efficiency, bioavailability, stability and/or acceptance by the patient.

These objectives are aimed to be achieved by providing a composition as described herein, by providing the composition for use in diseases, particular for the treatment of muscular dystrophy, disuse-related atrophy, cachexia or sarcopenia, as described herein and by providing a process to produce the composition as described herein.

Various embodiments of the invention are described herein.

Within certain aspects, provided herein is a pharmaceutical composition in solid oral dosage form comprising 0.01 to 15% (w/w) of (R)-7-(2-(1-(4-butoxyphenyl)-2-methylpropan-2-ylamino)-1-hydroxyethyl)-5-hydroxybenzo[d]thiazol-2(3H)-one and one or more pharmaceutically acceptable excipients, wherein (R)-7-(2-(1-(4-butoxyphenyl)-2-methylpropan-2-ylamino)-1-hydroxyethyl)-5-hydroxybenzo[d]thiazol-2(3H)-one is in acetate salt form.

In another embodiment, the invention provides a method for the manufacture of said pharmaceutical composition.

In another embodiment, the invention provides a method of treatment or prevention of muscular dystrophy, disuse-related atrophy, cachexia or sarcopenia comprising administering said pharmaceutical composition.

STATEMENT OF THE INVENTION

The compound of the invention is a selective beta-2 agonist. In particular, it shows an increased affinity for the beta-2 adrenoceptor which is greater than its affinity for the beta-1 adrenoceptor or the alpha-1A adrenoceptor, compared to known beta-2 agonists such as formoterol. Surprisingly, it also shows a lower affinity for the serotonin receptor ($5HT_{2C}$) and lower functional potency in $5HT_{2C}$ expressing cells than its racemate or its corresponding enantiomer, indicating that it does not affect locomotor activity and food intake which may cause body weight reduction, potentially counteracting beta-2 agonist-induced skeletal muscle hypertrophy. The negative effects of $5HT_{2C}$ receptor agonists on energy intake and body weight are described by J. Halford and J. Harrold in Handb Exp Pharmacol. 2012; (209) 349-56.

The composition of the present invention comprising the compound of the invention is therefore potentially useful in the treatment of a wide range of disorders, particularly in the treatment or prevention of muscle-wasting diseases such as muscular dystrophy, disuse-related atrophy, cachexia or sarcopenia.

The treatment of cachexia is also a contemplated use. All forms of cachexia are potentially treatable with the composition of the present invention, including cancer cachexia for example.

BRIEF DESCRIPTION OF FIGURES

FIG. 5 shows the X-ray powder diffraction pattern of the crystalline acetate salt of Compound A (compound of the invention).

DETAILED DESCRIPTION

Figure 1:
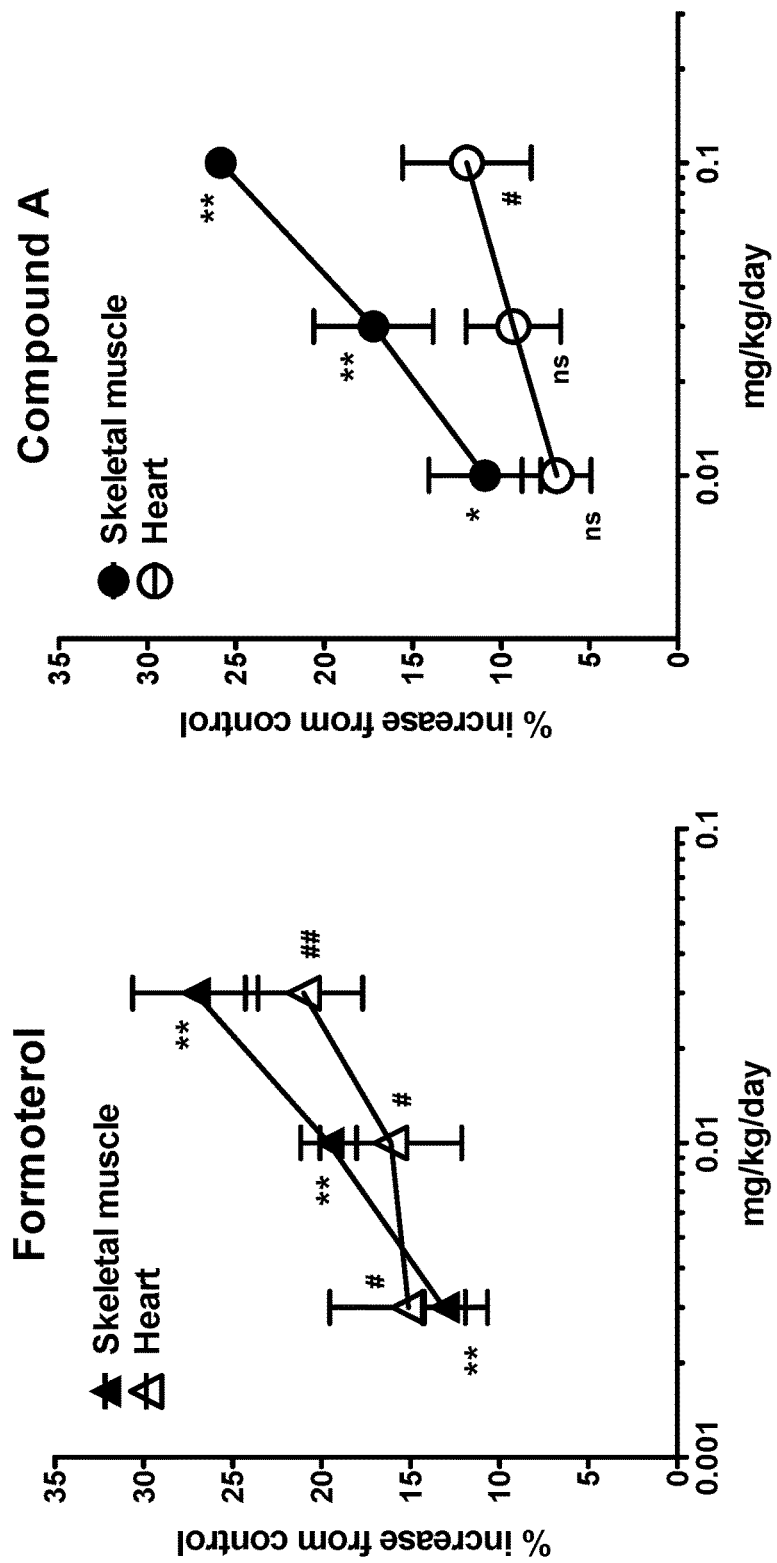
FIG. 1 shows the skeletal muscle mass and heart mass increase in rats injected with formoterol vs compound A (compound of the invention)–(values are expressed as means±SEM (n=5-6); pool of skeletal muscles (gastrocnemius-soleus-tibialis) normalized by initial body weight; heart weight normalized by brain weight.

The invention provides a pharmaceutical composition comprising (R)-7-(2-(1-(4-butoxyphenyl)-2-methylpropan-2-ylamino)-1-hydroxyethyl)-5-hydroxybenzo[d]thiazol-2(3H)-one and one or more pharmaceutically acceptable excipients.

In the following, unless specified otherwise, the terms have the following meaning.

A pharmaceutical composition as used herein is a mixture containing the active ingredient to be administered to a mammal, e.g., a human in order to prevent, treat or control a particular disease or condition affecting the mammal.

The term "pharmaceutically acceptable" as used herein refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

Typically, the term "active ingredient" refers to any compound, substance, drug, medicament, or active ingredient having a therapeutic or pharmacological effect, and which is suitable for administration to a mammal, e.g., a human, in a composition that is particularly suitable for oral administration.

In the pharmaceutical composition of the present invention, the active ingredient is (R)-7-(2-(1-(4-butoxyphenyl)-2-methylpropan-2-ylamino)-1-hydroxyethyl)-5-hydroxybenzo[d]thiazol-2(3H)-one.

As used herein, the term "compound A", "compound of the invention" or "compound of the present invention" refers to (R)-7-(2-(1-(4-butoxyphenyl)-2-methylpropan-2-ylamino)-1-hydroxyethyl)-5-hydroxybenzo[d]thiazol-2(3H)-one.

In the pharmaceutical compositions of the invention, the active ingredient (R)-7-(2-(1-(4-butoxyphenyl)-2-methylpropan-2-ylamino)-1-hydroxyethyl)-5-hydroxybenzo[d]thiazol-2(3H)-one is provided in the form of (R)-7-(2-(1-(4-butoxyphenyl)-2-methylpropan-2-ylamino)-1-hydroxyethyl)-5-hydroxybenzo[d]thiazol-2(3H)-one acetate salt.

As used herein, the absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Any asymmetric atom (e.g., carbon or the like) of a compound can be present in racemic or enantiomerically enriched, for example the (R)-, (S)- or (R,S)-configuration. The racemic 50:50 mixture of stereoisomers is designated as (R,S) and enantiomerically enriched forms by the enantiomeric excess of (R) to (S) respectively or (S) to (R) forms. The enantiomeric excess is represented usually by the equation ee=((m1−m2)/(m1+m2))*100% where m1 and m2 represent the mass of the respective enantiomeric forms R and S.

The compound of the present invention contains one asymmetric centre which is defined in terms of absolute stereochemistry as (R). Its corresponding enantiomer is defined as (S) which is the less active form.

In certain embodiments of the invention, the asymmetric atom has at least 95, 98 or 99% enantiomeric excess in the (R)-configuration.

In one embodiment of the invention, there is provided a pharmaceutical composition in solid oral dosage form comprising (R)-7-(2-(1-(4-butoxyphenyl)-2-methylpropan-2-ylamino)-1-hydroxyethyl)-5-hydroxybenzo[d]thiazol-2(3H)-one acetate salt, and one or more pharmaceutically acceptable excipients, wherein the (R)-7-(2-(1-(4-butoxyphenyl)-2-methylpropan-2-ylamino)-1-hydroxyethyl)-5-hydroxybenzo[d]thiazol-2(3H)-one acetate salt is present in at least 95% enantiomeric excess. In said embodiment, the composition preferably comprises 0.01-15% (w/w), more preferably 0.01-10% (w/w), even more preferably 0.01-5% (w/w), even more preferably 0.01-2% (w/w), most preferably 0.1-1% (w/w) of (R)-7-(2-(1-(4-butoxyphenyl)-2-methylpropan-2-ylamino)-1-hydroxyethyl)-5-hydroxybenzo[d]thiazol-2(3H)-one.

In one embodiment of the invention, there is provided a pharmaceutical composition in solid oral dosage form comprising (R)-7-(2-(1-(4-butoxyphenyl)-2-methylpropan-2-ylamino)-1-hydroxyethyl)-5-hydroxybenzo[d]thiazol-2(3H)-one acetate salt, and one or more pharmaceutically acceptable excipients, wherein the (R)-7-(2-(1-(4-butoxyphenyl)-2-methylpropan-2-ylamino)-1-hydroxyethyl)-5-hydroxybenzo[d]thiazol-2(3H)-one acetate salt is present in at least 98% enantiomeric excess. In said embodiment, the composition preferably comprises 0.01-15% (w/w), more preferably 0.01-10% (w/w), even more preferably 0.01-5% (w/w), even more preferably 0.01-2% (w/w), most preferably 0.1-1% (w/w) of (R)-7-(2-(1-(4-butoxyphenyl)-2-methylpropan-2-ylamino)-1-hydroxyethyl)-5-hydroxybenzo[d]thiazol-2(3H)-one.

In one embodiment of the invention, there is provided a pharmaceutical composition in solid oral dosage form comprising (R)-7-(2-(1-(4-butoxyphenyl)-2-methylpropan-2-ylamino)-1-hydroxyethyl)-5-hydroxybenzo[d]thiazol-2(3H)-one acetate salt, and one or more pharmaceutically acceptable excipients, wherein the (R)-7-(2-(1-(4-butoxyphenyl)-2-methylpropan-2-ylamino)-1-hydroxyethyl)-5-hydroxybenzo[d]thiazol-2(3H)-one acetate salt is present in at least 99% enantiomeric excess. In said embodiment, the composition preferably comprises 0.01-15% (w/w), more preferably 0.01-10% (w/w), even more preferably 0.01-5% (w/w), even more preferably 0.01-2% (w/w), most preferably 0.1-1% (w/w) of (R)-7-(2-(1-(4-butoxyphenyl)-2-methylpropan-2-ylamino)-1-hydroxyethyl)-5-hydroxybenzo[d]thiazol-2(3H)-one.

Depending on the choice of the starting materials and procedures for the chemical synthesis, compounds can be present in the form of one of the possible isomers or as mixtures thereof, for example as pure optical isomers, or as isomer mixtures, such as racemates. Optically active (R)- and (S)-isomers may be prepared using chiral synthons or chiral reagents, or resolved using conventional techniques. All tautomeric forms of the compound of the present invention are intended to be included.

Accordingly, as used herein the compound of the present invention can be in the form of tautomers or mixtures thereof.

Any resulting racemates of final products or synthesis intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compound of the present invention into its optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic or enantiomerically enriched products can also be resolved by chiral chromatography, e.g., high pressure liquid chromatography (HPLC) using a chiral adsorbent.

In the present invention, the pharmaceutical composition comprises (R)-7-(2-(1-(4-butoxyphenyl)-2-methylpropan-2-ylamino)-1-hydroxyethyl)-5-hydroxybenzo[d]thiazol-2(3H)-one in acetate salt form.

Pharmaceutically acceptable salts of the compound used in the present invention can be synthesized from a basic moiety, by conventional chemical methods. Generally, such salts can be prepared by reacting free base forms of the compound with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, $2^{nd}$ revised edition, 2011).

In an aspect of the present invention, the acetate salt of (R)-7-(2-(1-(4-butoxyphenyl)-2-methylpropan-2-ylamino)-1-hydroxyethyl)-5-hydroxybenzo[d]thiazol-2(3H)-one is formed by reacting (R)-7-(2-(1-(4-butoxyphenyl)-2-methylpropan-2-ylamino)-1-hydroxyethyl)-5-hydroxybenzo[d]thiazol-2(3H)-one with acetic acid in a suitable solvent.

In a certain aspect of the invention, the acetate salt of (R)-7-(2-(1-(4-butoxyphenyl)-2-methylpropan-2-ylamino)-1-hydroxyethyl)-5-hydroxybenzo[d]thiazol-2(3H)-one is formed according to the procedure described in example 3.

In a certain aspect of the invention, the acetate salt of (R)-7-(2-(1-(4-butoxyphenyl)-2-methylpropan-2-ylamino)-1-hydroxyethyl)-5-hydroxybenzo[d]thiazol-2(3H)-one is formed according to the procedure described in example 3a.

Unless stated otherwise, the concentration of active ingredient in the pharmaceutical composition of the invention is provided in w/w percentage of the free base of said active ingredient.

The pharmaceutical composition of the invention comprises 0.01 to 15% (w/w) of the active ingredient.

In one embodiment, it comprises 0.01 to 10% (w/w) of the active ingredient.

In one embodiment, it comprises 0.01 to 5% (w/w) of the active ingredient.

In one embodiment, it comprises 0.01 to 2% (w/w) of the active ingredient.

In one embodiment, it comprises 0.1 to 1% (w/w) of the active ingredient.

The compositions of the invention are suitable for oral administration.

Furthermore, the compound used in the present invention, including its acetate salt, may also be obtained in the form of its hydrates, or include other solvents used for its crystallization. The compound of the present invention may inherently or by design form solvates with pharmaceutically acceptable solvents (including water); therefore, it is intended that the invention embrace both solvated and unsolvated forms. The term "solvate" refers to a molecular complex of the compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Pharmaceutically acceptable solvates in accordance with the invention include those wherein the solvent of crystallization may be isotopically substituted, e.g. $D_2O$, $d_6$-acetone, $d_6$-DMSO.

The compound of the present invention, including its acetate salt, hydrates and solvates thereof, may inherently or by design form polymorphs.

The term "amorphous" describes a physical state which is not crystalline and may be verified by x-ray diffraction and other means including but not limited to observation with a polarized light microscope and differential scanning calorimetry.

The term "crystal" describes one form of the solid state of matter, which is distinct from a second form—the amorphous solid state, which exists essentially as an unorganized, heterogeneous solid. Crystals are regular three-dimensional array of atoms, ions, molecules, or molecular assemblies. Crystals are lattice arrays of building blocks called asymmetric units (which consist of the substance to be crystallized) that are arranged according to well-defined symmetries into unit cells that are repeated in three-dimensions.

The term "polymorph", as used herein, refers to crystalline forms having the same chemical composition but different spatial arrangements of the molecules, atoms, and/or ions forming the crystal.

In the present invention, the active ingredient may be in the form of polymorphs such as the polymorph described in example 4.

(R)-7-(2-(1-(4-butoxyphenyl)-2-methylpropan-2-ylamino)-1-hydroxyethyl)-5-hydroxybenzo[d]thiazol-2(3H)-one in acetate salt form used in the invention may be capable of forming co-crystals with suitable co-crystal formers. These co-crystals may be prepared from (R)-7-(2-(1-(4-butoxyphenyl)-2-methylpropan-2-ylamino)-1-hydroxyethyl)-5-hydroxybenzo[d]thiazol-2(3H)-one acetate salt by known co-crystal forming procedures. Such procedures include grinding, heating, co-subliming, co-melting, or contacting in solution (R)-7-(2-(1-(4-butoxyphenyl)-2-methylpropan-2-ylamino)-1-hydroxyethyl)-5-hydroxybenzo[d]thiazol-2(3H)-one acetate salt with the co-crystal former under crystallization conditions and isolating co-crystals thereby formed. Suitable co-crystal formers include those described in WO 2004/078163. A co-crystal refers to a crystalline material comprised of two or more unique solids at room temperature, each containing distinctive physical characteristics, such as structure, melting point and heats of fusion.

As used herein, a vehicle or carrier is a pharmaceutically acceptable composition that transports a drug across the biological membrane or within a biological fluid.

In one embodiment of the invention, there is provided a pharmaceutical composition in solid oral dosage form comprising (R)-7-(2-(1-(4-butoxyphenyl)-2-methylpropan-2-ylamino)-1-hydroxyethyl)-5-hydroxybenzo[d]thiazol-2(3H)-one acetate salt in crystalline form. In said embodiment, the composition preferably comprises 0.01-15% (w/w), more preferably 0.01-10% (w/w), even more preferably 0.01-5% (w/w), even more preferably 0.01-2% (w/w), most preferably 0.1-1% (w/w) of (R)-7-(2-(1-(4-butoxyphenyl)-2-methylpropan-2-ylamino)-1-hydroxyethyl)-5-hydroxybenzo[d]thiazol-2(3H)-one.

In another embodiment of the invention, there is provided a pharmaceutical composition in solid oral dosage form comprising crystalline (R)-7-(2-(1-(4-butoxyphenyl)-2-methylpropan-2-ylamino)-1-hydroxyethyl)-5-hydroxybenzo[d]thiazol-2(3H)-one acetate salt in substantially pure form. In said embodiment, the composition preferably comprises 0.01-15% (w/w), more preferably 0.01-10% (w/w), even more preferably 0.01-5% (w/w), even more preferably 0.01-2% (w/w), most preferably 0.1-1% (w/w) of (R)-7-(2-(1-(4-butoxyphenyl)-2-methylpropan-2-ylamino)-1-hydroxyethyl)-5-hydroxybenzo[d]thiazol-2(3H)-one.

As used herein, "substantially pure," when used in reference to crystalline (R)-7-(2-(1-(4-butoxyphenyl)-2-methylpropan-2-ylamino)-1-hydroxyethyl)-5-hydroxybenzo[d]thiazol-2(3H)-one acetate salt, means having a purity greater than 90 weight %, including greater than 90, 91, 92, 93, 94, 95, 96, 97, 98, and 99 weight %, and also including equal to about 100 weight % of (R)-7-(2-(1-(4-butoxyphenyl)-2-methylpropan-2-ylamino)-1-hydroxyethyl)-5-hydroxybenzo[d]thiazol-2(3H)-one acetate salt based on the weight of the compound.

The presence of reaction impurities and/or processing impurities may be determined by analytical techniques known in the art, such as, for example, chromatography, nuclear magnetic resonance spectroscopy, mass spectrometry, or infrared spectroscopy.

In another aspect, the invention relates to a pharmaceutical composition in solid oral dosage form comprising a crystalline form of the acetate salt of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with at least one, two or three peaks having angle of refraction 2 theta (θ) values selected from 8.8, 11.5, 16.4, 17.6, 18.2, 19.6, 20.1, 20.8, and 21.1° when measured using CuK$_\alpha$ radiation, more particularly wherein said values are plus or minus 0.2° 2θ.

In one embodiment, the invention relates to a pharmaceutical composition in solid oral dosage form comprising a crystalline form of the acetate salt of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with a peak at an angle of refraction 2θ value of 8.8° when measured using CuK$_\alpha$ radiation, more particularly wherein said value is plus or minus 0.2° 2θ.

In one embodiment, the invention relates to a pharmaceutical composition in solid oral dosage form comprising a crystalline form of the acetate salt of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with a peak at an angle of refraction 2θ value of 16.4° when measured using CuK$_\alpha$ radiation, more particularly wherein said value is plus or minus 0.2° 2θ.

In one embodiment, the invention relates to a pharmaceutical composition in solid oral dosage form comprising a crystalline form of the acetate salt of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with a peak at an angle of refraction 2θ value of 20.8° when measured using CuK$_\alpha$ radiation, more particularly wherein said value is plus or minus 0.2° 2θ.

In one embodiment, the invention relates to a pharmaceutical composition in solid oral dosage form comprising a crystalline form of the acetate salt of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern substantially the same as the X-ray powder diffraction pattern shown in FIG. 5 when measured using CuK$_\alpha$ radiation. For details see Example 4.

The term "substantially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

One of ordinary skill in the art will also appreciate that an X-ray diffraction pattern may be obtained with a measurement error that is dependent upon the measurement conditions employed. In particular, it is generally known that intensities in an X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of (R)-7-(2-(1-(4-butoxyphenyl)-2-methylpropan-2-ylamino)-1-hydroxyethyl)-5-hydroxybenzo[d]thiazol-2(3H)-one acetate salt is not limited to the crystal form that provides an X-ray diffraction pattern completely identical to the X-ray diffraction pattern depicted in the accompanying FIG. 5 disclosed herein. Any crystal forms that provide X-ray diffraction patterns substantially identical to those disclosed in the accompanying FIG. 5 fall within the scope of the present invention. The ability to ascertain substantial identities of X-ray diffraction patterns is within the purview of one of ordinary skill in the art.

As used herein, the term "a pharmaceutically acceptable excipient" refers to a pharmaceutically acceptable ingredient that is commonly used in the pharmaceutical technology for preparing granulate and/or solid oral dosage formulations. Examples of categories of excipients include, but are not limited to, binders, disintegrants, lubricants, glidants, fillers and diluents. One of ordinary skill in the art may select one or more of the aforementioned excipients with respect to the particular desired properties of the granulate and/or solid oral dosage form by routine experimentation and without any undue burden. The amount of each excipient used may vary within ranges conventional in the art. The following references which are all hereby incorporated by reference disclose techniques and excipients used to formulate oral dosage forms. See The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2000).

Typical excipients include antioxidants. Antioxidants may be used to protect ingredients of the composition from oxidizing agents that are included within or come in contact with the composition. Examples of antioxidants include water soluble antioxidants such as ascorbic acid, sodium sulfite, metabisulfite, sodium miosulfite, sodium formaldehyde, sulfoxylate, isoascorbic acid, isoascorbic acid, cysteine hydrochloride, 1,4-diazobicyclo-(2,2,2)-octane, and mixtures thereof. Examples of oil-soluble antioxidants include ascorbyl palmitate, butylated hydroxyanisole, butylated hydroxytoluene, potassium propyl gallate, octyl gallate, dodecyl gallate, phenyl-α-napthyl-amine, and tocopherols such as α-tocopherol.

Examples of pharmaceutically acceptable binders include, but are not limited to, starches; celluloses and derivatives thereof; copolymer of 1-vinyl-2-pyrrolidone and vinyl acetate; sucrose; dextrose; corn syrup; polysaccharides; and gelatin. Examples of celluloses and derivatives thereof include for example, microcrystalline cellulose, e.g., AVICEL PH from FMC (Philadelphia, Pa.), hydroxypropyl cellulose hydroxylethyl cellulose and hydroxylpropylmethyl cellulose METHOCEL from Dow Chemical Corp. (Midland, Mich.); HP-Cellulose 100 (Klucel LF). Copolymer of 1-vinyl-2-pyrrolidone and vinyl acetate can be purchased as Kollidon VA64 from BASF.

In the present invention, the binder may be present in an amount from about 1% to about 20% by weight of the composition.

Preferred binders for the pharmaceutical composition of the invention include HP-Cellulose 100 (Klucel LF) and copolymer of 1-vinyl-2-pyrrolidone and vinyl acetate.

Buffering agents may be used to maintain an established pH of the composition. Examples of buffering agents included sodium citrate, calcium acetate, potassium metaphosphate, potassium phosphate monobasic, and tartaric acid.

Bulking agents are ingredients which may provide bulk to a pharmaceutical composition. Examples of bulking agents include, without limitation, PEGs, mannitol, trehalose, lactose, sucrose, polyvinyl pyrrolidone, sucrose, glycine, cyclodextrins, dextran and derivatives and mixtures thereof.

Surfactants are agents used to stabilize multi-phasic compositions, e.g., used as wetting agents, antifoam agents, emulsifiers, dispersing agents, and penetrants. Surfactants can also be optionally used in the pharmaceutical composition of the invention. Surfactants include, but are not limited to, fatty acid and alkyl sulfonates; benzethanium chloride, e.g., HYAMINE 1622 from Lonza, Inc. (Fairlawn, N.J.); polyoxyethylene sorbitan fatty acid esters, e.g., the TWEEN Series from Uniqema (Wilmington, Del.); and natural surfactants, such as sodium taurocholic acid, 1-palmitoyl-2-Sn-glycero-3-phosphocholine, lecithin and other phospholipids. Such surfactants, e.g., minimize aggregation of lyophilized particles during reconstitution of the product. Surfactants, if present, are typically used in an amount of from about 0.01% to about 5% w/v.

A cosurfactant is a surface-active agent that acts in addition to the surfactant by further lowering the interfacial energy but that cannot form micellar aggregates by itself. Cosurfactants can be, for example, hydrophilic or lipophilic. Examples of a cosurfactant include, but are not limited to, cetyl alcohol and stearyl alcohol.

Examples of pharmaceutically acceptable disintegrants include, but are not limited to, starches, e.g. (sodium carboxymethyl starch); clays; celluloses, e.g. low substitute hydroxy propyl cellulose; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. In the present invention, the disintegrant may be present in an amount from about 1% to about 20% by weight of the composition.

Preferred disintegrants for the pharmaceutical composition of the invention include sodium carboxymethyl starch, low substitute hydroxy propyl cellulose, cross-linked sodium carboxymethylcellulose or croscarmellose sodium (e.g. AC-DI-SOL).

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. In the present invention, the filler and/or diluent may be present in an amount from about 15% to about 90% by weight of the composition.

Preferred fillers and/or diluents for the pharmaceutical composition of the invention include microcrystalline cellulose (e.g. Avicel PH101), spray-dried lactose, CA-HYD-Phosphate (e.g. Emcompress), mannitol DC (e.g. Compressol), pregelatinised starch (e.g. STA-RX 1500).

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. Typically, a lubricant may be present in an amount from about 0.1% to about 5% by weight of the composition; whereas, the glidant, e.g., may be present in an amount from about 0.1% to about 10% by weight. In the present invention, the lubricant is preferably present in the composition in an amount of 0.1 to 1% (w/w). In the present invention, the glidant is preferably present in the composition in an amount of 0.1 to 1% (w/w).

Preferred glidants of the pharmaceutical composition of the invention include Aerosil 200 and talc.

Preferred lubricants of the pharmaceutical composition of the invention include magnesium stearate.

The invention further provides pharmaceutical compositions that may comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Preservatives may also be used to protect the composition from degradation and/or microbial contamination. Examples of preservatives include liquipar oil, phenoxyethanol, methyl paraben, propyl paraben, butyl paraben, isopropyl paraben, isobutyl paraben, diazolidinyl urea, imidazolidinyl urea, diazolindyl urea, benzalkonium chloride, benzethonium chloride, phenol, and mixtures thereof (e.g., liquipar oil).

In one embodiment, the invention relates to a pharmaceutical composition in solid oral dosage form comprising
0.01 to 10% (w/w) (R)-7-(2-(1-(4-butoxyphenyl)-2-methylpropan-2-ylamino)-1-hydroxyethyl)-5-hydroxybenzo[d]thiazol-2(3H)-one;
15 to 90% (w/w) of at least one filler;
1 to 20% (w/w) of a disintegrant;
0.1 to 1% (w/w) of a glidant and
0.1 to 1% (w/w) of a lubricant.

In said embodiment, (R)-7-(2-(1-(4-butoxyphenyl)-2-methylpropan-2-ylamino)-1-hydroxyethyl)-5-hydroxybenzo[d]thiazol-2(3H)-one is provided in its acetate salt form.

In one embodiment, the invention relates to a pharmaceutical composition suitable for oral administration comprising
0.01 to 10% (w/w) (R)-7-(2-(1-(4-butoxyphenyl)-2-methylpropan-2-ylamino)-1-hydroxyethyl)-5-hydroxybenzo[d]thiazol-2(3H)-one;
15 to 90% (w/w) of at least one filler;
1 to 20% (w/w) of a binder;
1 to 20% (w/w) of a disintegrant;
0.1 to 1% (w/w) of a glidant and
0.1 to 1% (w/w) of a lubricant.

In said embodiment, (R)-7-(2-(1-(4-butoxyphenyl)-2-methylpropan-2-ylamino)-1-hydroxyethyl)-5-hydroxybenzo[d]thiazol-2(3H)-one is provided in its acetate salt form.

As used herein, the term "a therapeutically effective amount" of the compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease associated with beta-2-adrenoceptor activity; or (2) increasing or promoting the activity of beta-2-adrenoceptor.

In another non-limiting embodiment, the term "a therapeutically effective amount" refers to the amount of the compound of the present invention that, when administered to a cell, or a tissue, or a non-cellular biological material, or a medium, is effective to at least partially increase or promote the activity of beta-2-adrenoceptor. The meaning of the term "a therapeutically effective amount" as illustrated in the above embodiment for beta-2-adrenoceptor also applies by the same means to any other relevant proteins/peptides/enzymes, such as IGF-1 mimetics or ActRIIB/myostatin blockers and the like.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illustrate the invention and does not pose a limitation on the scope of the invention otherwise claimed.

(R)-7-(2-(1-(4-butoxyphenyl)-2-methylpropan-2-ylamino)-1-hydroxyethyl)-5-hydroxybenzo[d]thiazol-2(3H)-one can be prepared according to the Scheme provided infra.

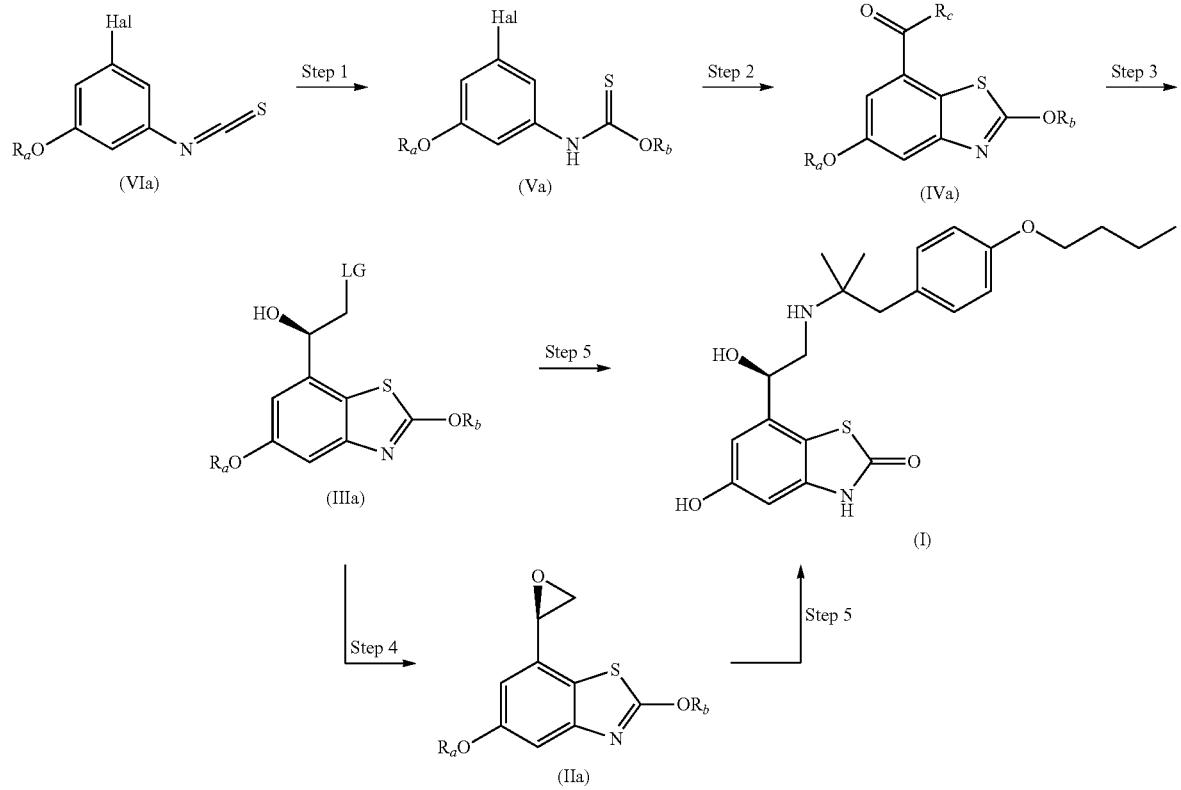

The process steps are described in more details below.

Step 1: A compound of formula (VIa) wherein Hal represents halogen and $R_a$ is a protecting group is reacted with a compound of formula $R_bOH$ wherein $R_b$ is a protecting group in the presence of a suitable base, e.g. triethylamine, to give a compound of formula (Va) wherein Hal represents halogen and $R_a$ and $R_b$ are protecting groups.

Step 2: A compound of formula (Va) is reacted with a suitable strong base, e.g. tert-butyllithium, in a suitable solvent, e.g. tetrahydrofuran (THF) in the presence of a suitable carbonylating agent, e.g. a suitable amide, to give a compound of formula (IVa) wherein $R_a$ and $R_b$ are protecting groups and $R_c$ is hydrogen or any moiety derived from the carbonylating agent.

Step 3: A compound of formula (IVa) is optionally functionalised prior to stereoselective conversion to give a compound of formula (IIIa) wherein $R_a$ and $R_b$ are protecting groups and LG is a leaving group.

Step 4: A compound of formula (IIIa) is treated with a suitable base, e.g. sodium bicarbonate, to give a compound of formula (IIa) wherein $R_a$ and $R_b$ are protecting groups.

Step 5: A compound of formula (IIa) or (IIIa) is reacted with 2-(4-butoxy-phenyl)-1,1-dimethyl-ethylamine in a suitable solvent e.g. toluene, optionally in the presence of a suitable base, e.g. potassium carbonate, followed by deprotection in the presence of a suitable acid, e.g. hydrochloric acid, to give a compound of formula (I).

The reactions can be effected according to conventional methods, for example as described in the Examples. The work-up of the reaction mixtures and the purification of the compounds thus obtainable may be carried out in accordance with known procedures. Acid addition salts may be produced from the free bases in known manner, and vice-versa. In particular, the acetate salt of (R)-7-(2-(1-(4-butoxyphenyl)-2-methylpropan-2-ylamino)-1-hydroxyethyl)-5-hydroxybenzo[d]thiazol-2(3H)-one can be prepared as described in examples 3 and 3a.

(R)-7-(2-(1-(4-butoxyphenyl)-2-methylpropan-2-ylamino)-1-hydroxyethyl)-5-hydroxybenzo[d]thiazol-2 (3H)-one can also be prepared by further conventional processes, for example as described in the Examples.

The starting materials used are known or may be prepared according to conventional procedures starting from known compounds, for example as described in the Examples.

The present processes may be modified, in which an intermediate product obtainable at any stage thereof is used as starting material and the remaining steps are carried out, or in which the starting materials are formed in situ under the reaction conditions, or in which the reaction components are used in the form of their salts or optically pure material.

The compound of the invention and intermediates can also be converted into each other according to methods generally known to those skilled in the art.

The pharmaceutical compositions of the present invention are in solid oral dosage form. Solid oral dosage forms include, but are not limited to, tablets, hard or soft capsules, caplets, lozenges, pills, mini-tablets, pellets, beads, granules (e.g. packaged in sachets), or powders. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Pharmaceutical compositions of the invention are preferably formulated for oral administration.

Suitable compositions for oral administration include an effective amount of a compound of the invention in acetate salt form in the form of tablets, hard or soft capsules, caplets, lozenges, pills, mini-tablets, pellets, beads, granules (e.g. packaged in sachets), or powders. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or *acacia*; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In one embodiment, the pharmaceutical composition of the invention is in the form of tablet or capsule.

In one embodiment, the pharmaceutical compositions are tablets or gelatin capsules comprising the active ingredient in acetate salt form together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, copolymers of 1-vinyl-2-pyrrolidone and vinyl acetate, sodium carboxymethylcellulose and/or polyvinylpyrrolidone; if desired
  d) disintegrants, e.g., starches, agar, alginic acid or its sodium salt, or effervescent mixtures; celluloses; cross-linked polymers; and/or
  e) absorbents, colorants, flavors and sweeteners.

Tablets may be either film coated or enteric coated according to methods known in the art.

Tablets can be optionally coated with a functional or non-functional coating as known in the art. Examples of coating techniques include, but are not limited to, sugar coating, film coating, microencapsulation and compression coating. Types of coatings include, but are not limited to, enteric coatings, sustained release coatings, controlled-release coatings.

Anhydrous pharmaceutical compositions and dosage forms can also be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

As used herein, a unit dosage form is a single dosage form which has the capacity of being administered to a subject to be effective, and which can be readily handled and packaged, remaining as a physically and chemically stable unit dose comprising the active ingredient.

Tablets may be manufactured by direct compression or granulation.

In the process of direct compression, the powdered materials included in the solid dosage form are typically compressed directly without modifying their physical nature. Usually, the active ingredient, excipients such as a glidant to improve the rate of flow of the tablet granulation, and lubricant to prevent adhesion of the tablet material to the surface of the dies and punches of the tablet press, are blended in a twin shell blender or similar low shear apparatus before being compressed into tablets.

Granulation is a process in which granulates are formed. These granulates are then subjected to direct compression in order to form a tablet or encapsulated for a capsule. The granulates may be formed by wet granulation which includes:
a) forming a powder mixture of the active ingredient and at least one pharmaceutically acceptable excipient;
b) adding a granulation liquid to the powder blend under agitation to form a wet mass;
c) granulating the wet mass to form moist granulates;
d) drying the moist granulates to form granulates;
e) sieving the granulates.

Alternatively, the granulates may be formed by fluid-bed granulation which includes:
a) suspending particles of a material (e.g., an inert material or the active ingredient) with, e.g., a rising airstream in a vertical column;
b) spraying a granulating material into the column;
c) allowing the particles to be coated with the granulating material resulting in granulates.

Another alternative for producing granulates includes melt granulation. This process includes:
a) forming a mixture of a active ingredient with at least one release retardant, e.g. a release retarding polymer, and optionally, a plasticizer;
b) granulating the mixture using an extruder or other suitable equipment, for example a jacketed high shear mixer, while heating the mixture to a temperature above the softening temperature of the release retardant; as used herein, the "softening temperature" refers to the temperature at which the release retardant experiences a change in the rate of viscosity decrease as a function of temperature; and
c) cooling the granules to room temperature, for example, at a controlled rate.

Another alternative for producing granulates includes dry granulation which may include roller compaction or slugging. Roller compaction is a process in which uniformly mixed powders are compressed between two counter-rotating roll pairs to form a compressed sheet or ribbon that is then milled (granulated). Slugging is a process in which uniformly mixed powders are compressed into large tablets which are subsequently comminuted into the desired size.

In a preferred embodiment of the process of the invention, granulates are produced by roller compaction.

Capsules as used herein refer to a formulation in which the active ingredient in acetate salt form may be enclosed in either a hard or soft, soluble container or shell, often formed from gelatin.

A hard gelatin capsule, also known as a dry-filled capsule, is composed of two sections, one slipping over the other, thus completely surrounding (encapsulating) the drug formulation.

A soft elastic capsule has a soft, globular, e.g., gelatin shell.

In one embodiment, the invention relates to a process of making a pharmaceutical composition suitable for oral administration comprising the steps of:
a) mixing (R)-7-(2-(1-(4-butoxyphenyl)-2-methylpropan-2-ylamino)-1-hydroxyethyl)-5-hydroxybenzo[d]thiazol-2(3H)-one acetate salt with a filler and a glidant to form a pre-mix;
b) mixing the pre-mix obtained in step a) with a further filler and a disintegrant to obtain a powder;
c) adding a lubricant to the powder obtained in step b) to obtain a final blend and
d) processing the final blend obtained in step c) into a pharmaceutical composition suitable for oral administration.

In one embodiment, the invention provides a process of making a pharmaceutical composition suitable for oral administration in the form of a capsule comprising the steps of:
a) mixing (R)-7-(2-(1-(4-butoxyphenyl)-2-methylpropan-2-ylamino)-1-hydroxyethyl)-5-hydroxybenzo[d]thiazol-2(3H)-one acetate salt with a filler and a glidant to form a pre-mix;
b) mixing the pre-mix obtained in step a) with a further filler and a disintegrant to obtain a powder;
c) adding a lubricant to the powder obtained in step b) to obtain a final blend and
d) encapsulating the final blend in a capsule to provide said pharmaceutical composition.

In one embodiment, the invention provides a process of making a pharmaceutical composition suitable for oral administration in the form of a tablet comprising the steps of:
a) mixing (R)-7-(2-(1-(4-butoxyphenyl)-2-methylpropan-2-ylamino)-1-hydroxyethyl)-5-hydroxybenzo[d]thiazol-2(3H)-one acetate salt with a filler and a glidant to form a pre-mix;
b) mixing the pre-mix obtained in step a) with a further filler and a disintegrant to obtain a powder;
c) adding a lubricant to the powder obtained in step b) to obtain a final blend and
d) compressing the final blend obtained in step c) to a tablet.

In one embodiment, the invention provides a process of making a pharmaceutical composition suitable for oral administration in the form of a tablet comprising the steps of:
a) mixing (R)-7-(2-(1-(4-butoxyphenyl)-2-methylpropan-2-ylamino)-1-hydroxyethyl)-5-hydroxybenzo[d]thiazol-2(3H)-one acetate salt with a filler and a glidant to form a pre-mix;
b) mixing the pre-mix obtained in step a) with a further filler, a binder and a disintegrant to obtain a powder;
c) adding a lubricant to the powder obtained in step b) to obtain an intermediate blend;
d) compacting the intermediate blend and milling the compacted material;
e) mixing the milled material obtained in step d) with a further aliquot of glidant and disintegrant and adding a further aliquot of lubricant to obtain a final blend and
f) compressing the final blend obtained in step e) to a tablet.

In a preferred embodiment of said process, compacting is carried out by roller compaction.

In the processes of the invention, all mixing steps may be preceded by a sieving step.

In the processes of the invention, the amount of (R)-7-(2-(1-(4-butoxyphenyl)-2-methylpropan-2-ylamino)-1-hydroxyethyl)-5-hydroxybenzo[d]thiazol-2(3H)-one acetate salt is preferably such that 0.01-15% (w/w), more preferably 0.01-10% (w/w), even more preferably 0.01-5% (w/w), even more preferably 0.01-2% (w/w), most preferably 0.1-1% (w/w) of (R)-7-(2-(1-(4-butoxyphenyl)-2-methylpropan-2-ylamino)-1-hydroxyethyl)-5-hydroxybenzo[d]thiazol-2(3H)-one is present in the pharmaceutical composition.

The active ingredient in the present pharmaceutical composition may be released once administered to a subject in different ways.

Release retardants are materials that slow the release of an active ingredient from a pharmaceutical composition when orally ingested. Various sustained release systems, as known in the art, can be accomplished by the use of a release retarding component, e.g., a diffusion system, a dissolution system and/or an osmotic system.

For example, the pharmaceutical composition may be designed for immediate release which refers to the rapid release of the majority of the active ingredient, e.g., greater than about 50%, about 60%, about 70%, about 80%, or about 90% within a relatively short time, e.g., within 1 hour, 40 minutes, 30 minutes or 20 minutes after oral ingestion. Particularly useful conditions for immediate-release are release of at least or equal to about 80%, e.g. up to 99%, of the active ingredient within thirty minutes after oral ingestion. The particular immediate release conditions for a specific active ingredient will be recognized or known by one of ordinary skill in the art.

Alternatively, a modified release such as controlled release or delayed release of the active ingredient may be desirable. Controlled release refers to the gradual but sustained release over a relatively extended period of the active ingredient content after oral ingestion. The release will continue over a period of time and may continue through until and after the pharmaceutical composition reaches the intestine.

A delayed release may refer to the release of the active ingredient that does not start immediately when the pharmaceutical composition reaches the stomach but is delayed for a period of time, for instance, until when the pharmaceutical composition reaches the intestine when the increasing pH is used to trigger release of the active ingredient from the pharmaceutical composition.

Another alternative includes chronopharmaceutic release which refers to the release of an active ingredient at a rhythm or timepoint that matches the biological requirement of a given disease therapy.

(R)-7-(2-(1-(4-butoxyphenyl)-2-methylpropan-2-ylamino)-1-hydroxyethyl)-5-hydroxybenzo[d]thiazol-2(3H)-one in free form or in pharmaceutically acceptable salt form, exhibits valuable pharmacological properties, e.g. beta-2-adrenoceptor modulating properties, e.g. as indicated in in vitro and in vivo tests as provided in the next sections and is therefore indicated for therapy or for use as research chemicals, e.g. as a tool compound.

(R)-7-(2-(1-(4-butoxyphenyl)-2-methylpropan-2-ylamino)-1-hydroxyethyl)-5-hydroxybenzo[d]thiazol-2(3H)-one may be useful in the treatment of an indication selected from: muscular dystrophy, disuse-related atrophy, cachexia or sarcopenia.

Thus, as a further embodiment, the present invention provides the pharmaceutical composition as defined herein, as a medicament. In an embodiment, the present invention relates to the pharmaceutical composition as defined herein for use as a medicament. In a further embodiment, the present invention relates to the pharmaceutical composition as defined herein for use in the treatment or prevention of muscular dystrophy, disuse-related atrophy, cachexia or sarcopenia.

Thus, as a further embodiment, the present invention provides the use of the pharmaceutical composition as defined herein in therapy. In a further embodiment, the therapy is selected from a disease which may be treated by activation of beta-2-adrenoceptor. In another embodiment, the disease is selected from muscular dystrophy, disuse-related atrophy, cachexia or sarcopenia.

In another embodiment, the invention provides a method of treating a disease which is treated by activation of beta-2-adrenoceptor comprising administration of the pharmaceutical composition as defined herein. In a further embodiment, the disease is selected from muscular dystrophy, disuse-related atrophy, cachexia or sarcopenia.

A further aspect of the invention thus relates to a method of treatment or prevention of muscular dystrophy, disuse-related atrophy, cachexia or sarcopenia comprising administering the pharmaceutical composition as defined herein to a subject in need thereof.

The utility of the pharmaceutical composition of the present invention may be observed in standard clinical tests, including bioavailability tests, in, for example, known indications of drug dosages giving therapeutically effective blood levels of the active ingredient; for example using dosages in the range of 0.01-15 mg of active ingredient per day for a 75 kg mammal, e.g., adult human and in standard animal models.

The pharmaceutical composition, e.g., in form of a tablet or capsule or in the form of a powder suitable for tablet or capsule formulation may suitably and appropriately contain at least 0.01-15 mg of the active ingredient, preferably 0.5-1.5 mg of the active ingredient. In one embodiment, the solid oral dosage form will contain about 1 mg of the active ingredient compound. Such unit dosage forms are suitable for administration one to two times daily depending upon the particular purpose of therapy, the phase of therapy and the like.

The therapeutically effective dosage of a compound or a pharmaceutical composition, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compound of the present invention can be applied in vitro in the form of solutions, e.g., aqueous solutions, and in vivo either enterally, parenterally, advantageously subcutaneously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.01-500 mg/kg, or between about 0.01-100 mg/kg, or between about 0.01-1 mg/kg, or between about 0.01-0.1 mg/kg.

The activity of the compound of the present invention can be assessed by the following in vitro method. Further in vivo methods are described further in the Examples.

Test 1: In Vitro Cellular Functional Assay Using CHO Cells and Skeletal Muscle Cells cAMP:

Human skeletal muscle cells (skMC) were obtained from Cambrex (catalog no CC-2561) and cultured in Skeletal Basal Medium (SKBM) obtained from Cambrex (catalog no #CC-3161). The cAMP responses were measured using cAMP dynamic 2 bulk HTRF-Assay kit obtained from Cisbio or Cis Competitive Intelligence (catalog no 62AM4PEC). skMC cells were cultured for 1 day in SKBM cell culture medium supplemented with 20% FCS in 384-well plates at 37° C., 5% $CO_2$. The next day, the cells were washed twice with 50 μL PBS, and differentiated for 3 days in serum-free SKBM in presence of 1 μM SB431542, a ALK 4/5 Inhibitor obtained from Sigma (catalog no S4317) at 37° C., 7.5% $CO_2$. On day 4, serum-free SKBM supplemented with 1 μM SB431542 was removed, cells were washed twice with 50 μL PBS and further differentiated for 1 day in serum-free SKBM without SB431542 (50 μL per well) at 37° C., 7.5% $CO_2$. Rat skMC and cardiomyocytes cells were isolated from neonatal rats in a standard way and treated as described above. Chinese hamster ovary (CHO) cells stably transfected with human β adrenoceptors (β1 or β2) were produced at Novartis Institutes for BioMedical Research and cultured as described before (J Pharmacol Exp Ther. 2006 May; 317(2):762-70).

Compounds were made up in stimulation buffer at 2× required concentration and 1:10 serial dilutions in stimulation buffer were prepared in 96-well plate (U-form). DMSO control was normalized to the DMSO content of the highest dilution, e.g. 0.1% DMSO (×2) for $10^{-5}$ M (×2) concentration of the first compound dilution. The assay was carried out in 384-well plates, in a 20 μL stimulation volume, and a final assay volume of 40 μL per well. On the day of experiment, culture medium was removed from 384-well cell culture plates by inverting and flicking the plate on stack of paper 2-3 times. 10 μL of fresh culture medium per well was first added in the 384-well plate. After 10 minutes of incubation at room temperature, 10 μL per well of working compounds dilutions were added to the cells and incubated for 30 minutes at room temperature in the dark. During this time, working solutions of reagents were prepared by diluting stock solutions of anti cAMP cryptate and cAMP D2 1:20 in lysis buffer, supplied with the kit. After 30 minutes of compound incubation, 10 μL of cAMP-D2 and 10 μL of anti cAMP cryptate were sequentially added to the assay plates. After 1 hour of incubation time at room temperature in the dark, the measurement was performed with the PheraStar (Excitation wavelength: 337 nm, Emission wavelengths: 620 and 665 nm).

$Ca^{2+}$:

The human adrenergic Alpha1A CHO-K1 cell line was purchased from Perkin Elmer (ValiScreen™ Stable recombinant GPCR Cell line, catalog no ES-036-C, Lot no M1W-C1, Boston, Mass., USA). One day before the experiment, Alpha1A frozen cells (10 millions per ml and per vial) were thawed in a water bath at 37° C. The cell suspension was centrifuged for 5 minutes at 1,000 rpm and the cell pellet was resuspended in cell culture medium. Cells were seeded into black 384-well plates with clear bottom at a density of 8,000 cells per well in 50 μL of cell culture medium. Plates were incubated for about 24 hours at 37° C., 5% $CO_2$. The day of the experiment, the medium was removed using a cell washer (TECAN PW3). After the final wash there was 10 μL left in the wells. 40 μL of loading buffer were added and cells were loaded for 60 min at 37° C., 5% $CO_2$. Plates were washed with TECAN PW3 with 20 μL assay buffer left and were incubated for at least 20 minutes at RT before performing the FLIPR experiment. Compounds were then characterized in the agonist and/or antagonist mode. For assay validation, the same protocol was used with the fresh cells. In this case, cells were detached from a 150 $cm^2$ flask using 3 ml of Trypsin-EDTA, centrifuged and resuspended in cell culture medium.

Cells were stimulated by adding 5 μL of compounds (5×), using the FLIPR head. Compounds acting as agonists induce a transient increase of intracellular calcium. This was recorded on the FLIPR system. A measurement of the signal baseline was first recorded every second for 2 minutes before the injection of the compounds. Calcium measurements were performed by exciting the cells with the argon ion laser at 488 nm at 0.6 W laser power and recording the fluorescence signal with a CCD camera (opening of 0.4 sec) for 2 minutes. Low controls (unstimulated cells) were determined with the addition of 5 μL of assay buffer. High controls were determined with the addition of 5 μL of a known agonist at high concentration $EC_{100}$ (A-61603 at 1 μM) and a reference agonist compound was also added in each plate.

The compound of the invention exhibits efficacy in test assay 1 with an $EC_{50}$ of less than 10 nM. Specific activity is shown in example 6.

Further specific activities of the compound of the invention are described in examples 7 to 11.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesise the compound of the present invention are either commercially available or can be produced by organic synthesis methods known to one of ordinary skill in the art (Houben-Weyl 4th Ed. 1952, Methods of Organic Synthesis, Thieme, Volume 21). Further, the compound of the present invention can be produced by organic synthesis methods known to one of ordinary skill in the art as shown in the following examples.

EXAMPLES

List of Abbreviations 1M one molar
APCI atmospheric-pressure chemical ionization
aq aqueous
AR adrenoceptor
atm atmosphere
br broad
cm centimeters
d doublet
dd double doublet
ddd double double doublet
$(DHDQ)_2PHAL$ Hydroquinidine 1,4-phthalazinediyl diether
DMAC dimethylacetamide
DMSO dimethylsulfoxide
DSC differential scanning calorimetry
ee enantiomeric excess equiv equivalent
ES electron-spray
g grams
h hours
HPLC high performance liquid chromatography
HRMS high resolution mass spectroscopy
m multiplet
MC methyl cellulose
mbar millibar
MeOH methanol
min minutes
ml milliliters
MS mass spectroscopy
MTBE methyl tert-butyl ether
nm nanometers
NMR nuclear magnetic resonance
RT retention time
r.t. room temperature
s singlet
sat. saturated
sept septet
t triplet
TFA trifluoroacetic acid
μm micrometers
w/v weigh/volume
XRPD x-ray powder diffraction Unless otherwise indicated, HPLC/MS spectra were recorded on an Agilent 1100 series LC/Agilent MS 6210 Quadrupole. A Waters Symmetry C8 column (3.5 um; 2.1× 50 mm) (WAT200624) was used. The following gradient method was applied (%=percent by volume): A=water+ 0.1% TFA/B=acetonitrile+0.1% TFA; 0.0-2.0 min 90A: 10B-5A: 95B; 2.0-3.0 min 5A: 95B; 3.0-3.3 min 5A: 95B-90A: 10B; flow 1.0 ml/min; column temperature 50° C. All compounds were ionized in APCI mode.

$^1$H-NMR spectra were recorded on a Varian Mercury (400 MHz) or Bruker Advance (600 MHz) machine.

Optical rotation was measured on a Perkin Elmer Polarimeter 341.

LCMS Condition for Example 2b, 2c, 2d, 2e, 2g:

Mass spectra station: Agilent 6130 quadrupole LC/MS with Agilent 1200 HPLC; Column: Agilent Zorbax SB-C18 (Rapid resolution), 2.1*30 mm, 3.5 μm; Mobile phases: B: 0.1% formic acid in water; C: 0.1% formic acid in MeCN; 1.0 min to 6.0 min, 95% B to 5% B, and 5% C to 95% C; 6.0 min to 9.0 min, 5% B and 95% C; post time: 2.0 min; flow rate: 0.8 ml/min; column temperature: 30° C.; UV detection: 210 nm and 254 nm; MS scan positive and negative: 80-1000; Ionization method: API-ES.

HRMS Conditions for Example 2f:

Instrument: Waters Acquity UPLC coupled with Synapt Q-TOF MS; Column: Waters Acquity UPLC BEH C18, 2.1*50 mm, 1.7 μm Mobile Phase: A: 0.1% formic acid in water, B: 0.1% formic acid in Acetonitrile; Column temperature: at room temperature; UV detection: scan from 190 nm to 400 nm; Flow rate: 0.5 mL/min;

| Gradient condition: | | |
| --- | --- | --- |
| Time [min.] | Phase B [%] | |
| 0 | 5 | |
| 1 | 5 | Start of acquisition |
| 9 | 95 | |
| 11 | 95 | End of acquisition |
| 11.10 | 5 | |
| 14 | 5 | Next injection |

Ionization method: ESI+; MS scan range: 100-1000 m/z.

Intermediate A:
2-(4-butoxyphenyl)-1,1-dimethyl-ethylamine a) 4-(2-methyl-2-nitropropyl)phenol A mixture of 4-(hydroxymethyl)phenol (20 g), KOtBu (27.1 g) and DMAC (200 mL) was stirred with magnetic stirrer. 2-nitropropane (21.5 g) was added slowly within 20 min. The mixture was heated to 140° C. for 5 hr before cooled to r.t. The mixture was added slowly to cool HCl aqueous solution (3.0%, 600 mL), then extracted with MTBE (300 ml*1, 200 ml*1). The organic layers were combined, washed with water (300 ml*2) and sat. NaCl aqueous solution (50 ml*1), then dried with anhydrous Na$_2$SO$_4$. The mixture was filtered and concentrated under vacuum to give light-yellow solid (28.5 g), which was used for next step without further purification.

[M−1]$^+$=194.2; RT=5.3 minutes $^1$H-NMR (400 MHz, CDCl$_3$) ppm 6.96 (d, J=8.5 Hz, 2H), 6.75 (d, J=8.5 Hz, 2H), 3.11 (s, 2H), 1.56 (s, 6H).

b) 1-butoxy-4-(2-methyl-2-nitropropyl)benzene

The mixture of 4-(2-methyl-2-nitropropyl)phenol (20.4 g), 1-bromobutane (28.7 g), DMAC (200 ml), K$_2$CO$_3$ (21.6 g), tetrabutylammonium iodide (38.7 g) was stirred with magnetic stirrer and heated to 85° C. for 17 h. The mixture was cooled to 0-10° C. and water (700 ml) was added. The mixture was extracted with MTBE (300 ml*1, 200 ml*1). The combined organic phases were washed with water (250 ml*2), then concentrated under vacuum to give a red-brown oil (27.8 g), which was used in the next step without further purification.

$^1$H-NMR (400 MHz, CDCl$_3$) ppm 7.0 (d, J=8.8 Hz, 2H), 6.81 (d, J=8.8 Hz, 2H), 3.93 (t, J=6.6 Hz, 2H), 3.12 (s, 2H), 1.74 (m, 2H), 1.56 (s, 6H), 1.48 (m, 2H), 0.97 (t, 3H).

c) 2-(4-butoxyphenyl)-1,1-dimethyl-ethylamine

In a hydrogenating reactor (1 L), a solution of 1-butoxy-4-(2-methyl-2-nitropropyl) benzene (27.8 g) in AcOH (270 ml) was added followed by wet Raney Ni (7.0 g). The mixture was purged with H$_2$ for 3 times, then heated to 60° C. and kept stirring under 5.0 atm for 16 h. The mixture was filtered, the total filtrate was concentrated under vacuum. The resulting residue was diluted with water (150 ml)/n-heptane (80 ml), the aqueous layer was washed with n-heptane (80 ml) again. The aqueous layer was adjusted with NaOH (~20%) to pH~11, then extracted with MTBE (100 ml*1) and EtOAc (150 ml*2). The medium layer was discarded. All top layers were combined and washed with saturated NaHCO$_3$ (100 ml) and saturated NaCl (100 ml) before being dried with anhydrous Na$_2$SO$_4$. After filtration, the mixture was concentrated. The resulting residual was stirred and HCl solution in isopropyl alcohol (2M, 40 ml) was added. The slurry was heated to 60° C. and n-heptane (120 ml) was added. The mixture was cooled to 20° C., then filtered, the cake was washed with some n-heptane. The white solid was dried in air for 2 days to give 10 g of pure HCl salt of product. Yield: 35.2%.

[MH]+=222.2; RT=5.0 minutes $^1$H-NMR (400 MHz, d-DMSO) ppm 8.13 (s, 3H), 7.12 (d, J=8.6 Hz, 2H), 6.88 (d, J=8.5 Hz, 2H), 3.93 (t, J=6.4 Hz, 2H), 2.80 (s, 2H), 1.67 (m, 2H), 1.42 (m, 2H), 1.18 (s, 6H), 0.92 (t, 3H).

Example 1

(R)-7-(2-(1-(4-butoxyphenyl)-2-methylpropan-2-ylamino)-1-hydroxyethyl)-5-hydroxybenzo[d]thiazol-2(3H)-one

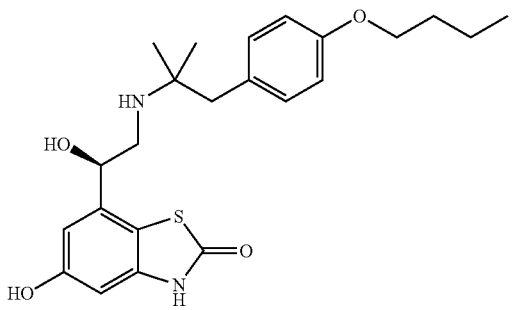 [SMILES: CCCCOc1ccc(CC(C)(C)NC[C@H](O)c2cc(O)cc3[nH]c(=O)sc23)cc1]

a) 1-tert-Butoxy-3-fluoro-5-isothiocyanatobenzene

Thiophosgene (33.6 g) in CHCl$_3$ (250 ml) and K$_2$CO$_3$ (64.7 g) in H$_2$O (450 ml) are added, separately and simultaneously, drop wise to a solution of 3-tert-Butoxy-5-fluoro-phenyl-amine (42.9 g) in CHCl$_3$ (350 ml) at 0° C. The reaction mixture is warmed to room temperature over night. The organics are separated and washed with water (3×), brine (1×), dried over MgSO$_4$, filtered and the solvent removed in vacuo. The title compound is obtained by flash column chromatography (silica, eluent dichloromethane/iso-hexane 1:3).

$^1$H NMR (CDCl$_3$, 400 MHz); 6.70 (m, 3H), 1.40 (s, 9H).

b) (3-tert-Butoxy-5-fluoro-phenyl)-thiocarbamic acid O-isopropyl ester 1-tert-Butoxy-3-fluoro-5-isothiocyanatobenzene (24.0 g) and triethylamine (10.9 g) are dissolved in iso-propanol (150 ml). The reaction mixture is refluxed for 18 hours and the solvent is removed by vacuo. The crude product is dissolved in hexane: diethyl ether (19:1). The diethyl ether is removed in vacuo and the solution is cooled to 0° C. for 3 hours. The solution is filtered to give the title compound.

$^1$H NMR (CDCl$_3$, 400 MHz); 8.10 (br s, 1H), 6.65 (br s, 2H), 6.45 (ddd, 1H) 5.60 (sept, 1H), 1.35 (d, 6H), 1.30 (s, 9H).

c) 5-tert-Butoxy-2-isopropoxy-benzothiazole-7-carbaldehyde (3-tert-Butoxy-5-fluoro-phenyl)-thiocarbamic acid O-isopropyl ester (2.2 g) is dissolved in dry tetrahydrofuran (20 ml) The reaction mixture is cooled to −78° C. and tert-butyl lithium (15.2 ml, of 1.5 M solution) is added over 20 minutes. The reaction mixture is then warmed to −10° C. for 75 minutes. The reaction mixture is then re-cooled to −78° C., N,N-dimethyl-formamide (1.5 g) is added and the reaction mixture is slowly warmed to room temperature then stirred at −10° C. for 1 hour. The reaction mixture is quenched with HCl$_{(aq)}$ (5 ml, of a 2 M solution), the organics are separated between ethyl acetate/water and removed in vacuo. The title compound is obtained by flash column chromatography (silica, eluent ethyl acetate/iso-hexane 1:9).

MS (ES+) m/e 294 (MH$^+$).

d) 5-tert-Butoxy-2-isopropoxy-7-vinylbenzothiazole

Ph$_3$PMe.Br (5.0 g) is dissolved in dry tetrahydrofuran (100 ml) under argon. N-butyl lithium (8.8 ml, of 1.6 M solution) is added at room temperature over 10 minutes and reaction mixture stirred for a further 30 minutes. A solution of 5-tert-Butoxy-2-isopropoxy-benzothiazole-7-carbaldehyde (1.25 g) in dichloromethane (40 ml) is added drop wise to the reaction mixture and the reaction mixture is stirred for 4.5 hours at room temperature. The solvent is removed in vacuo, redissolved in ethyl acetate, washed with water (3×), brine (1×), dried over MgSO$_4$, filtered and the solvent removed in vacuo. The title compound is obtained by flash column chromatography (silica, eluent ethyl acetate/iso-hexane 1:9).

MS (ES+) m/e 292 (MH$^+$).

e) (R)-1-(5-tert-Butoxy-2-isopropoxy-benzothiazol-7-yl)-ethane-1,2-diol

K$_3$Fe(CN)$_6$ (1.2 g), K$_2$CO$_3$ (0.5 g), (DHQD)$_2$PHAl (19 mg) are dissolved in tert-butanol/water (15 ml, 1:1 mix) under argon and stirred for 15 minutes. The reaction mixture is cooled to 0° C. and OsO$_4$ (3.1 mg) is added followed by 5-tert-Butoxy-2-isopropoxy-7-vinylbenzothiazole (0.35 g). The reaction mixture is stirred over night at room temperature. The reaction mixture is quenched with sodium-meta-bisulphate (1 g) and stirred for 1.5 hours. Ethyl acetate is added, the organics are separated, washed with (2×) water, (1×) brine, dried over MgSO$_4$, filtered and the solvent removed in vacuo. The title compound is obtained by flash column chromatography (silica, eluent ethyl acetate/iso-hexane 2:5).

MS (ES+) m/e 326 (MH$^+$).

f) (R)-2-(5-tert-butoxy-2-isopropoxybenzo[d]thiazol-7-yl)-2-hydroxyethyl-4-methylbenzenesulfonate Into a 500-ml 3-necked round-bottom flask, purged and maintained with an inert atmosphere of nitrogen, was placed a solution of (R)-1-(5-tert-butoxy-2-isopropoxy-benzo[d]thiazol-7-yl)ethane-1,2-diol (20 g, 59.05 mmol) in pyridine (240 ml) and 4 Å molecular sieves (5 g). This was followed by the addition of a solution of toluenesulfonic acid chloride (tosyl chloride) (15.3 g, 79.73 mmol) in pyridine (60 ml) dropwise with stirring at 0° C. The resulting solution was stirred for 4 h at room temperature. The reaction was then quenched by the addition of 1000 ml of 1M hydrogen chloride. The resulting solution was extracted with 2×300 ml of ethyl acetate and the organic layers are combined. The organic phase was washed with 1×500 ml of 1M hydrogen chloride, 1×500 ml of 10% sodium bicarbonate and 300 ml of brine. The mixture was dried over anhydrous sodium sulfate and concentrated under vacuum. The residue was applied onto a silica gel column with ethyl acetate/petroleum ether (1:10). This resulted in 26 g (87%) of (R)-2-(5-tert-butoxy-2-isopropoxybenzo[d]thiazol-7-yl)-2-hydroxyethyl 4-methylbenzenesulfonate as yellow oil.

LC/MS R$_T$=2.47 min; (m/z): 480 [M+H]$^+$ $^1$H-NMR: (400 MHz, DMSO-d$_6$): δ (ppm) 7.57 (d, 2H); 7.36 (d, 2H); 7.17 (d, 1H); 6.79 (d, 1H); 6.32 (d, 1H); 5.37-5.26 (m, 1H); 4.97-4.90 (m, 1H); 4.12-4.00 (m, 2H); 2.40 (s, 3H); 1.45-1.38 (m, 6H); 1.32 (s, 9H).

g) (R)-1-(5-tert-butoxy-2-isopropoxybenzo[d]thiazol-7-yl)-2-(1-(4-butoxyphenyl)-2-methylpropan-2-ylamino)ethanol Into a 1000-mLml 4-necked round-bottom flask was placed a solution of (R)-2-(5-tert-butoxy-2-isopropoxybenzo[d]thiazol-7-yl)-2-hydroxyethyl-4-methylbenzenesulfonate (26 g, 51.55 mmol, 1.00 equiv) in toluene (320 mLml) and 2-(4-butoxyphenyl)-1,1-dimethyl-ethylamine (intermediate A) (22 g, 99.47 mmol, 1.93 equiv). The solution was stirred for 24 h at 90° C. in an oil bath. The resulting mixture was concentrated under vacuum. The residue is applied onto a silica gel column with ethyl acetate/petroleum ether (1:8). This resulted in 16 g (58%) of (R)-1-(5-tert-butoxy-2-isopropoxybenzo[d]thiazol-7-yl)-2-(1-(4-butoxyphenyl)-2-methylpropan-2-ylamino)ethanol as light yellow oil.

LC/MS: $R_T$=2.24 min (m/z): 529 [M+H]$^+$ $^1$H-NMR: (600 MHz, DMSO-d$_6$): δ (ppm) 7.12 (s, 1H); 6.83 (d, 2H); 6.77 (s, 1H); 6.63 (d, 2H); 5.80 (br. s, 1H); 5.38-5.30 (m, 1H); 4.70-4.66 (m, 1H); 3.90 (t, 2H); 2.81-2.61 (m, 2H); 2.50-2.39 (m, 2H); 1.71-1.62 (m, 2H); 1.47-1.41 (m, 2H); 1.41 (d, 6H); 1.22 (s, 9H); 0.91 (q, 3H); 0.88 (s, 3H); 0.83 (s, 3H).

h) (R)-7-(2-(1-(4-butoxyphenyl)-2-methylpropan-2-ylamino)-1-hydroxyethyl)-5-hydroxybenzo[d]thiazol-2(3H)-one A solution of (R)-1-(5-tert-butoxy-2-isopropoxybenzo[d]thiazol-7-yl)-2-(1-(4-butoxyphenyl)-2-methylpropan-2-ylamino)ethanol (3.5 g) in formic acid (40 ml) was stirred for 68 h at ambient temperature. 50 ml of water was added, and the resulting mixture was evaporated to dryness (rotary evaporator, 15 mbar, 40° C.) to give 3.8 g of crude product. This material was partitioned between saturated aqueous sodium bicarbonate (50 ml) and ethyl acetate (50 ml) in order to remove formic acid. The aqueous layer was extracted 3× with ethyl acetate (30 ml each). The combined organic extracts were dried over magnesium sulfate, filtered and concentrated to give 3 g of crude free-base. This material was flash-chromatographed (silica gel; gradient 0-60% methanol in dichloromethane). Pure fractions were collected and evaporated to dryness to give 1.74 g of an amorphous semi-solid.

This material was subjected to chiral preparative chromatography [column: Chiralpak IC (20 um) 7.65×37.5 cm; eluent: n-heptane/dichloromethane/ethanol/diethylamine 50:30:20 (+0.05 diethylamine); flow rate=70 ml/min; concentration: 2.5 g/50 ml eluent; detection: UV, 220 nm] to give pure enantiomer (100% ee).

This material was dissolved in 45 ml of acetonitrile at 60° C. The solution was allowed to cool to ambient temperature over 18 h, upon which precipitation occurred. The mixture was diluted with 5 ml of cold (4° C.) acetonitrile and filtered through a Buchner funnel. The filter cake was washed twice with cold acetonitrile. Then the wet solid was collected and dried in vacuo (0.2 mbar) at ambient temperature overnight to give 1.42 g of (R)-7-(2-(1-(4-butoxyphenyl)-2-methylpropan-2-ylamino)-1-hydroxyethyl)-5-hydroxybenzo[d]thiazol-2(3H)-one as a colorless powder.

LC/MS: $R_T$=1.81 min (m/z): 431 [M+H]$^+$ $^1$H-NMR: (600 MHz, DMSO-d$_6$): δ (ppm) 11.5 (br. s, 1H); 9.57 (br. s, 1H); 6.99 (d, 2H); 6.76 (d, 2H); 6.52 (s, 1H); 6.47 (s, 1H); 5.63 (br. s, 1H); 4.53-4.48 (m, 1H); 3.90 (t, 2H); 2.74-2.63 (m, 2H); 2.54-2.45 (m, 2H); 1.71-1.62 (m, 2H); 1.49-1.40 (m, 2H); 0.93 (q, 3H); 0.89 (s, 6H).

Optical rotation: $[\alpha]_D^{22}$=−43° (c=1.0 g/100 ml MeOH).

Example 2

Alternative route to (R)-7-(2-(1-(4-butoxyphenyl)-2-methylpropan-2-ylamino)-1-hydroxyethyl)-5-hydroxybenzo[d]thiazol-2(3H)-one

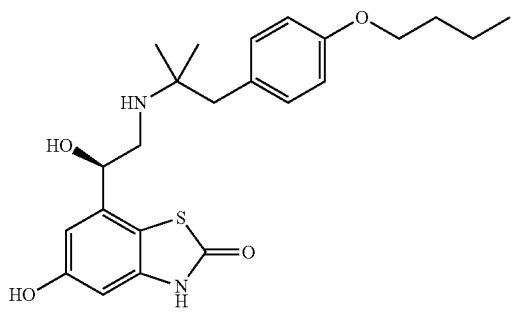 [SMILES: CCCCOc1ccc(CC(C)(C)NC[C@H](O)c2cc(O)cc3[nH]c(=O)sc23)cc1]

a) 1-tert-Butoxy-3-fluoro-5-isothiocyanato-benzene 1,1'-Thiocarbonyldiimidazole (423 g, 2.37 mol) was dissolved in dichloromethane (3200 ml). The mixture was stirred under N$_2$ atmosphere while a solution of 3-tert-butoxy-5-fluoroaniline (435 g, 2.37 mol) in dichloromethane (800 ml) was added slowly within 2 h. Then the mixture was kept stirring at 20° C. for 16 h. The mixture was diluted with water (3000 ml). The separated dichloromethane phase was washed again with water (3000 ml) before dried with anhydrous Na$_2$SO$_4$ for 2 h. The mixture was filtered and the filtrate was concentrated under vacuum to remove solvent to give 1-tert-butoxy-3-fluoro-5-isothiocyanato-benzene (499 g).

$^1$H-NMR (400 MHz, CDCl$_3$): 6.63-6.68 (m, 3H), 1.37 (s, 9H).

b) (3-tert-Butoxy-5-fluoro-phenyl)-thiocarbamic acid O-isopropyl ester

To a solution of 1-tert-butoxy-3-fluoro-5-isothiocyanato-benzene (460 g, 2.04 mol) in anhydrous isopropyl alcohol (3250 ml) was added triethylamine (315 g, 3.06 mol). The mixture was heated to reflux under N$_2$ atmosphere for 16 h and the temperature was cooled to 40-50° C. After concentration, the resulting dark residue was diluted with n-heptane (1000 ml) and heated to 60° C. The mixture was slowly cooled to 25° C., at the same time seeding was added. A slurry was observed and stirred at 25° C. for 16 h before being cooled slowly to 0-10° C. within 2 h. After filtration and washing with n-heptane (200 ml), the collected solid was dried in oven under vacuum at 40-45° C. for 18 h to give (3-tert-Butoxy-5-fluoro-phenyl)-thiocarbamic acid O-isopropyl ester (453.1 g).

LCMS: [M+H]$^+$=286.1; RT=7.2 minutes $^1$H-NMR (400 MHz, CDCl$_3$): 8.18 (s, 1H), 6.81 (m, 2H), 6.51 (dt, J=10.2 Hz, 1H), 5.66 (heptet, J=6.3 Hz, 1H), 1.42 (d, J=6.2 Hz, 6H), 1.37 (s, 9H).

c) 1-(5-tert-Butoxy-2-isopropoxy-benzothiazol-7-yl)-2-chloro-ethanone

Under a nitrogen atmosphere, a solution of tert-butyl-lithium (481 ml, 737.6 mmol, 1.6 M) was added dropwise to a solution of (3-tert-Butoxy-5-fluoro-phenyl)-thiocarbamic acid O-isopropyl ester (200 g, 700.83 mmol) in 2-Me-THF (1600 ml) at temperature below −65° C. The reaction temperature was warmed to −35° C., and a second portion of tert-butyllithium (388 ml, 737.6 mmol, 1.9 M) was added slowly while keeping the temperature below −35° C. The reaction mixture was then stirred at this temperature for 3 h and cooled down to −70° C. A solution of N-methyl-N-methoxy chloroacetamide (96.4 g, 700.83 mmol) in 2-MeTHF (300 ml) was added to the reaction mixture while keeping the temperature below −70° C. The mixture was then warmed to −30° C. and stirred for 45 minutes. The cold reaction mixture was quenched by dropwise addition of 30% HCl in isopropanol (240 g) followed by the addition of 1500 ml water. The organic layer was washed sequentially with 1000 ml water, 1500 ml saturated aqueous $NaHCO_3$ and 1500 ml brine. After concentration, the resulting light brown residue was added to isopropanol (135 ml). The mixture was warmed to 50° C. and cooled down slowly to 25° C. n-heptane (135 ml) was added dropwise to the solution and the mixture was stirred overnight. The slurry was filtered and the filter cake was washed with n-heptane (40 ml) followed by another portion of n-heptane (20 ml). The cake was dried under vacuum to yield 1-(5-tert-butoxy-2-isopropoxy-benzothiazol-7-yl)-2-chloro-ethanone as off-white powder (42.8 g, 17.9% yield).

$^1$H NMR (400 MHz, $CDCl_3$): 7.60 (d, J=2.0 Hz, 1H), 7.45 (d, J=2.0 Hz, 1H), 5.40 (heptet, J=6.3 Hz, 1H), 4.77 (s, 2H), 1.47 (d, J=6.3 Hz, 6H), 1.40 (s, 9H).

LCMS: [M+H]$^+$=342.1, RT=7.29 min.

d) (R)-1-(5-tert-Butoxy-2-isopropoxy-benzothiazol-7-yl)-2-chloro-ethanol

A suspension of 1-(5-tert-butoxy-2-isopropoxybenzo[d]thiazol-7-yl)-2-chloro-ethanone (70 g, 204.8 mmol) and RuCl(p-cymene)[(S,S)-Ts-DPEN] (1.954 g, 3.07 mmol) in methanol/DMF (1330 ml/70 ml) was degassed and refilled with $N_2$ three times. A degassed preformed mixture of formic acid (28.3 g) in $Et_3N$ (124.3 g) was added slowly while keeping the internal temperature between 15 to 20° C. The resulting yellow suspension was warmed up to 30° C. After 2 h the reaction mixture is cooled to 25° C., water (750 ml) was then added into the reaction mixture followed by the addition of acetic acid (56 ml) in one portion. The mixture was concentrated and then diluted with TBME (1000 ml). Aqueous phase was separated and extracted with TBME (1000 ml). The combined organic phase was washed sequentially with water and brine and then dried with $Na_2SO_4$ and concentrated under vacuum to give (R)-1-(5-tert-Butoxy-2-isopropoxy-benzothiazol-7-yl)-2-chloro-ethanol (72 g).

LCMS (method A): [M+H]$^+$=343.1, RT=5.67 min.

$^1$H NMR (400 MHz, $CDCl_3$): 7.29 (d, J=2.0 Hz, 1H), 6.83 (d, J=2.0 Hz, 1H), 5.37 (heptet, J=6.3 Hz, 1H), 4.96 (m, 1H), 3.74 (m, 2H), 3.01 (s, 1H), 1.46 (d, J=6.2 Hz, 6H), 1.36 (s, 9H).

e) (R)-5-tert-Butoxy-2-isopropoxy-7-oxiranyl-benzothiazole

To a solution of (R)-1-(5-tert-butoxy-2-isopropoxybenzo[d]thiazol-7-yl)-2-chloro-ethanol (140 g, 407.1 mmol) in TBME (420 ml) was added dropwise NaOH aqueous solution (2M, 420 ml) followed by tetrabutylammonium iodide (7.52 g, 20.36 mmol) added in one portion. After 4 h at 26° C., 400 ml TBME was added and the organic layer was separated. The aqueous layer was extracted with TBME (400 ml). The combined organic layers were washed with water (400 ml) and brine (400 ml) to give (R)-5-tert-butoxy-2-isopropoxy-7-oxiranyl-benzothiazole (122 g).

LCMS: [M+H]$^+$=308.0, RT=6.80 min.

$^1$H NMR (400 MHz, $CDCl_3$) ppm 7.28 (d, J=2.0 Hz, 1H), 6.85 (d, J=2.0 Hz, 1H), 5.38 (m, 1H), 3.96 (m, 1H), 3.15 (dd, J=4.3, 5.5 Hz, 1H), 2.94 (dd, J=4.3, 5.5 Hz, 1H), 1.45 (d, J=Hz, 6H), 1.37 (s, 9H).

f) (R)-1-(5-tert-butoxy-2-isopropoxybenzo[d]thiazol-7-yl)-2-(1-(4-butoxyphenyl)-2-methylpropan-2-ylamino)ethanol (R)-5-tert-butoxy-2-isopropoxy-7-oxiranyl-benzothiazole (145 g, 471.7 mmol) and 2-(4-butoxy-phenyl)-1,1-dimethyl-ethylamine (114.8 g, 518.9 mmol) were dissolved in DMSO (850 ml). The reaction mixture was heated to 80° C. and stirred for 27 h. The mixture was then cooled to 25° C. and added to a stirred mixture of water (1500 ml) and TBME (1500 ml). The aqueous layer was separated and extracted with TBME (1000 ml). The combined organic layers were sequentially washed with water (1500 ml) and brine (1000 ml), dried with anhydrous $Na_2SO_4$. After concentration, the residue was purified by column chromatography (eluting with 10% of EtOAc in n-heptane to 33% of EtOAc in n-heptane). Solid product (R)-1-(5-tert-butoxy-2-isopropoxybenzo[d]thiazol-7-yl)-2-(1-(4-butoxyphenyl)-2-methylpropan-2-ylamino)ethanol was obtained (140 g) as off-white solid.

HRMS: [M+1] 529.2996

$^1$H NMR (400 MHz, $CDCl_3$): 7.26 (m, 1H), 7.01 (m, 1H), 6.99 (m, 1H), 6.78-6.80 (m, 3H), 5.39 (m, 1H), 4.65 (dd, J=3.8, 8.8 Hz, 1H), 3.83 (t, J=6.4 Hz, 2H), 2.96 (dd, J=3.8, 12 Hz, 1H), 2.74 (dd, J=8.8, 12 Hz, 1H), 2.60 (dd, J=13.6, 17.6 Hz, 2H), 1.72-1.79 (m, 2H), 1.50 (m, 2H), 1.46 (d, J=2.0 Hz, 3H), 1.45 (d, J=2.0 Hz, 3H), 1.35 (s, 9H), 1.06 (s, 3H), 1.04 (s, 3H), 0.98 (t, J=7.2 Hz, 3H).

g) (R)-7-(2-(1-(4-butoxyphenyl)-2-methylpropan-2-ylamino)-1-hydroxyethyl)-5-hydroxybenzo[d]thiazol-2(3H)-one To (R)-1-(5-tert-butoxy-2-isopropoxybenzo[d]thiazol-7-yl)-2-(1-(4-butoxyphenyl)-2-methylpropan-2-ylamino)ethanol (7.5 g) in isopropanol (30 ml) and water (25 ml) was added 1M HCl aqueous solution (43 ml). The reaction mixture was then heated to 60° C. and stirred for 2.5 h. The mixture was cooled to 50° C., and then 2M NaOH aqueous solution (18 ml) was added slowly to adjust pH between 8.2-8.4. The reaction mixture was then cooled to 30° C., followed by extraction with TBME (first time with 40 ml, the second time with 25 ml). Two organic layers were combined and washed with water (38 ml for two times) before drying with anhydrous $Na_2SO_4$. After filtration, the filtrate was concentrated, and then dissolved in MeCN (145 ml). The solution was treated with active carbon (0.6 g) and heated to 60° C. After a second filtration, the cake was washed with MeCN (10 ml for two times), the filtrate was crystallized at 60° C. to gain (R)-7-(2-(1-(4-butoxyphenyl)-2-methylpropan-2-ylamino)-1-hydroxyethyl)-5-hydroxy-benzo[d]thiazol-2(3H)-one (3.8 g). e.e. =97.6%.

LCMS (method A): [M+H]$^+$=431.2

$^1$H NMR (400 MHz, DMSO-$d_6$): 9.5 (br. s, 1H), 6.81 (d, J=8.5 Hz, 2H), 6.57 (d, J=8.6 Hz, 2H), 6.33 (d, J=2.2 Hz, 1H), 6.30 (d, J=2.2 Hz, 1H), 4.43 (br. s, 1H), 3.69 (t, J=6.4 Hz, 2H), 2.58-2.59 (m, 2H), 2.24-2.31 (m, 2H), 1.41-1.48 (m, 2H), 1.15-1.25 (m, 2H), 0.78 (s, 6H), 0.70 (t, J=7.4 Hz, 3H).

Example 3

(R)-7-(2-(1-(4-butoxyphenyl)-2-methylpropan-2-ylamino)-1-hydroxyethyl)-5-hydroxybenzo[d]thiazol-2(3H)-one acetate salt 500 mg (1.161 mmol) of free base (R)-7-(2-(1-(4-butoxyphenyl)-2-methylpropan-2-ylamino)-1-hydroxyethyl)-5-hydroxybenzo[d]thiazol-2(3H)-one was suspended in 10.0 ml acetonitrile and 0.25 ml water in a 50 ml four-necked flask and paddle stirred at r.t. The suspension was heated at an internal temperature of 50° C. (jacket temperature 75° C.) and 72 mg acetic acid (1.161 mmol) was added (a clear yellow solution was formed). The solution was cooled down over 30 min. at r.t. and 0.15 ml water added.

The solution was then seeded with (R)-7-(2-(1-(4-butoxyphenyl)-2-methylpropan-2-ylamino)-1-hydroxyethyl)-5-hydroxybenzo[d]thiazol-2(3H)-one acetate and stirred overnight (16 h) at r.t. The suspension was then filtered at r.t. through a glass filer and washed three times with 1 ml acetonitrile. 510 mg of wet filter cake was dried in a drying oven overnight (16 h) at r.t. to dryness. Yield: 508 mg white powder (89.1%)

Preparation of (R)-7-(2-(1-(4-butoxyphenyl)-2-methylpropan-2-ylamino)-1-hydroxyethyl)-5-hydroxybenzo[d]thiazol-2(3H)-one acetate seeds 57.0 mg (0.132 mmol) of free base (R)-7-(2-(1-(4-butoxyphenyl)-2-methylpropan-2-ylamino)-1-hydroxyethyl)-5-hydroxybenzo[d]thiazol-2(3H)-one and 8.03 mg (0.132 mmol) acetic acid were dissolved in 1.0 ml acetonitrile and 0.05 ml water. The solution was stirred at r.t. with a magnetic stirrer stirred. Precipitation took place over night. The solution was then filtered at r.t. through a glass filter and washed three times with 0.5 ml acetonitrile. The wet filter cake was dried in a drying oven overnight (16 h) at r.t. to dryness. Yield: 57 mg white powder

Example 3a

Alternative procedure for the formation of (R)-7-(2-(1-(4-butoxyphenyl)-2-methylpropan-2-ylamino)-1-hydroxyethyl)-5-hydroxybenzo[d]thiazol-2(3H)-one acetate salt (R)-1-(5-tert-butoxy-2-isopropoxybenzo[d]thiazol-7-yl)-2-(1-(4-butoxyphenyl)-2-methylpropan-2-ylamino)ethanol, (1 equiv.) was suspended in isopropanol. At 50 to 60°, a 1M aqueous hydrochloric acid solution (3 equiv.) was added within about 30-60 min. After complete reaction (approximately 2.5 hours at 60° C.) the solution was cooled to 20° C. and sodium hydroxide 2M (3 equiv.) added gradually at this temperature. After complete addition the emulsified free base (R)-7-(2-(1-(4-butoxyphenyl)-2-methylpropan-2-ylamino)-1-hydroxyethyl)-5-hydroxybenzo[d]thiazol-2(3H)-one was extracted into ethylacetate and the organic layer washed with water. The organic layer was treated with activated carbon and filtered using microcrystalline cellulose as a filter aid. The filter cake was washed with ethyl acetate. The filtrate, containing the free base (R)-7-(2-(1-(4-butoxyphenyl)-2-methylpropan-2-ylamino)-1-hydroxyethyl)-5-hydroxybenzo[d]thiazol-2(3H)-one, was carefully concentrated to a defined residual volume by distillation at a jacket temperature of 55° C. under reduced pressure. Isopropylacetate was then added and partly removed by distillation to a defined residual volume at a jacket temperature of 55° C. under reduced pressure. Further isopropylacetate and a solution of acetic acid in isopropylacetate were added to the warm distillation residue at 50-55° C. During the acetic acid addition the batch was seeded with (R)-7-(2-(1-(4-butoxyphenyl)-2-methylpropan-2-ylamino)-1-hydroxyethyl)-5-hydroxybenzo[d]thiazol-2(3H)-one acetate salt to initiate the controlled crystallization of the acetate salt early at 50-55° C. After gradually cooling to 0° C. the product suspension was filtered and washed twice with cold isopropylacetate. The filter cake was dried at 50 to 90° C. under reduced pressure until constant weight to give crystalline (R)-7-(2-(1-(4-butoxyphenyl)-2-methylpropan-2-ylamino)-1-hydroxyethyl)-5-hydroxybenzo[d]thiazol-2(3H)-one acetate salt at a typical yield of approximately 80%.

Example 4

XRPD and DSC analysis of crystalline (R)-7-(2-(1-(4-butoxyphenyl)-2-methylpropan-2-ylamino)-1-hydroxyethyl)-5-hydroxybenzo[d]thiazol-2(3H)-one acetate salt form XRPD analysis of crystalline (R)-7-(2-(1-(4-butoxyphenyl)-2-methylpropan-2-ylamino)-1-hydroxyethyl)-5-hydroxybenzo[d]thiazol-2(3H)-one acetate salt form was carried out under the following experimental conditions:

| XRPD method | |
| --- | --- |
| Instrument | Bruker D8 Advance (reflection) |
| Irradiation | CuKα (40 kV, 30 mA) |
| Step | 0.017grd |
| Scan type | Continuous scan |
| Scan time | 107.1 s |
| Scan range | 2°-40° (2 theta value) |

DSC analysis was carried out under the following experimental conditions:

| DSC method | |
| --- | --- |
| Instrument | Perkin Elmer Diamond |
| Temperature range | 30°-300 C. |
| Sample mass | 2-3 mg |
| Sample pan | Aluminium closed |
| Nitrogen flow | 20-50 K/min |

XRPD analysis of crystalline (R)-7-(2-(1-(4-butoxyphenyl)-2-methylpropan-2-ylamino)-1-hydroxyethyl)-5-hydroxybenzo[d]thiazol-2(3H)-one acetate salt Crystalline (R)-7-(2-(1-(4-butoxyphenyl)-2-methylpropan-2-ylamino)-1-hydroxyethyl)-5-hydroxybenzo[d]thiazol-2(3H)-one acetate salt was analysed by XRPD and the characteristic peaks are shown in the table below (see also FIG. 6). Of these, the peaks at 8.8, 11.5, 16.4, 17.6, 18.2, 19.6, 20.1, 20.8, and 21.1° 2-theta are the most characteristic.

| Angle (2-Theta °) | Intensity % |
| --- | --- |
| 8.8 | high |
| 10.0 | low |
| 11.5 | high |
| 14.2 | low |
| 14.6 | low |
| 15.7 | low |
| 16.4 | high |
| 17.6 | medium |

-continued

| Angle (2-Theta °) | Intensity % |
|---|---|
| 18.2 | high |
| 19.1 | low |
| 19.6 | medium |
| 20.1 | high |
| 20.8 | high |
| 21.1 | medium |
| 23.3 | medium |
| 26.2 | low |
| 26.6 | medium |
| 27.1 | medium |

Crystalline (R)-7-(2-(1-(4-butoxyphenyl)-2-methylpropan-2-ylamino)-1-hydroxyethyl)-5-hydroxybenzo[d]thiazol-2(3H)-one acetate salt was analysed by DSC and found to have a broad endotherm at around 170° C.

Example 5

Comparative Solubilities of Free Base, Acetate Salt and Glycolate Salt Forms of Compound A The relative solubilities of the free base form and the acetate and glycolate salt forms of Compound A were analysed and the results are show in the table below. Solutions were titrated with addition of HCl or NaOH for pH adjustment. The improved aqueous solubilities of the acetate and glycolate salt forms relative to the free base form of Compound A make the acetate and glycolate salts of Compound A more suitable for subcutaneous injection or infusion.

| Compound A free base solubility in H$_2$O | | Compound A acetate salt solubility in H$_2$O | | Compound A glycolate salt solubility in H$_2$O | |
|---|---|---|---|---|---|
| pH | Conc in mg/mL | pH | Conc in mg/mL | pH | Conc in mg/mL |
| 6.2 | 0.27 | 5.9 | 1.33 | 5.1 | 13.1 |
| 7.0 | 0.05 | 6.0 | 1.11 | 5.3 | 6.39 |
| 7.3 | <0.01 | 6.1 | 1.10 | 5.4 | 4.47 |
| 7.8 | <0.01 | 6.2 | 0.55 | | |

Example 6

In Vitro Cellular Profiles of Compound of the Invention (Compound A), its Enantiomer (Compound B), its Racemate (Compound A/B) and Formoterol The compound of the invention (compound A) shows the following EC$_{50}$ values in Test 1 as described hereinbefore.

| | CHO cells[#] | | | Primary cells; cAMP response EC$_{50}$ (E$_{max}$ %) | | |
|---|---|---|---|---|---|---|
| | EC$_{50}$ (E$_{max}$ %) | | | Human | Rat | Rat |
| Compounds | β2 AR | β1 AR | α1A AR | skMC | skMC | cardiomyocytes |
| Formoterol | 0.7 nM (99%**) | 85 nM (86%**) | 190 nM | 0.2 nM (96%*) | 0.9 nM | 2.9 nM |
| Compound A (R) | 5.6 nM (88%**) | 560 nM (32%**) | >10 µM | 0.7 nM (96%*) | 3.4 nM (98%*) | 5.7 nM (71%**) |
| Compound B (S) | 950 nM (83%**) | >10 µM | >30 µM | 280 nM (100%*) | n.d. | n.d. |
| Compound A/B | 11 nM (87%**) | 684 nM (38%**) | n.d. | 0.63 nM (100%*) | n.d. | n.d. |
| Compound A (R) acetate salt | 2.5 nM (91%) | n.d. | n.d. | 1.7 nM (93%) | n.d. | n.d. | skMC: differentiated skeletal myotubes;
*compared to formoterol;
**compared to isoprenaline;
[#]cAMP for β1 and β2, Ca$^{2+}$ for α1A;
n.d. not determined The compound of the invention (compound A) is a potent and selective β2 AR agonist with very low intrinsic efficacy on β1 AR and no activity on α1A AR. Its enantiomer Compound B is very weak on β2 AR with an EC$_{50}$ of 950 nM.

Example 7

Effects of Formoterol and Compound A on Skeletal Muscle and Heart Weight In vivo Male Wistar Han IGS (International Genetic Standard) rats (Crl:WI(Han)) at the weight of 350-400 g were purchased from Charles River Laboratories. Rats were acclimated to the facility for 7 days. Animals were housed in groups of 3 animals at 25° C. with a 12:12 h light-dark cycle. They were fed a standard laboratory diet containing 18.2% protein and 3.0% fat with an energy content of 15.8 MJ/kg (NAFAG 3890, Kliba, Basel, Switzerland). Food and water were provided ad libitum. Formoterol or Compound A was dissolved in the vehicle indicated below to achieve a dose range of 0.003 to 0.03 mg/kg/day for formoterol and 0.01 to 0.1 mg/kg/day for Compound A with the Alzet model 2ML4 for 28 days. Pumps were filled with the solution and kept for several hours at 37° C. in PBS until surgical implantation. Rats were treated subcutaneously with Temgesic at a dose of 0.02 mg/kg with a volume of 1 ml/kg at least 30 minutes before surgery, and then the pumps filled with the solution indicated above were implanted subcutaneously into the back of the rats under anesthesia with isoflurane at a concentration of 3%. Temgesic was administered subcutaneously to the rats 24 h and 48 h after the surgery. Body weights were measured twice per week. Clips were removed 10 days after the surgery under anesthesia. Four weeks after the treatment, the rats were euthanized with $CO_2$, and the tibialis anterior, gastrocnemius and soleus muscles, heart and brain were dissected and weighed. Brain weight was used for normalization of organ weights. Results are expressed as mean +/−SEM. Statistical analysis was carried out using Dunnett's multiple comparison test following one-way analysis of variance to compare the treatment groups to the vehicle control group. Differences were considered to be significant when the probability value was <0.05:*: Statistical analyses were performed by GraphPad Prism version 5.0 (GraphPad Software, Inc., La Jolla, Calif.). Muscle weight was normalized to the body weight at day 0 (initial body weight) and heart weight was normalized by brain weight.

Study 1: Formoterol

| Group | Treatment | Dose (mg/kg) | Route | Regimen |
|---|---|---|---|---|
| 1 | Vehicle* | 0 | s.c. | Alzet |
| 2 | Formoterol | 0.003 | | minipump |
| 3 | Formoterol | 0.01 | | 2ML4 for 4 |
| 4 | Formoterol | 0.03 | | weeks |

*Vehicle: 20% 1:2 Cremophor:Ethanol in saline (0.9% NaCl)

Study 2: Compound A

| Group | Treatment | Dose (mg/kg) | Route | Regimen |
|---|---|---|---|---|
| 1 | Vehicle* | 0 | s.c. | Alzet |
| 2 | Compound A | 0.01 | | minipump |
| 3 | Compound A | 0.03 | | 2ML4 for 4 |
| 4 | Compound A | 0.1 | | weeks |

*Vehicle: 20% 1:2 Cremophor:Ethanol in saline (0.9% NaCl)

FIG. 1 shows that formoterol induces both skeletal muscle hypertrophy and heart mass increase to the same extent, while Compound A induces skeletal muscle hypertrophy with minimum impact on heart mass, indicating that Compound A exhibits a selective effect on skeletal muscle over cardiac muscle. Compound A significantly induces skeletal muscle hypertrophy by 11% at 0.01 mg/kg/day with steady state plasma concentration of ~0.2 nM, while there were no findings on the heart histopathology even at 0.1 mg/kg/day with steady state concentration of ~2 nM.

Example 8

Effects of Formoterol and Compound A on the Function of Isolated Organs (Left Atrium Contraction, Sino-Atrial Node Beating Rate and Automaticity of Whole Heart)

Method

Left Atrium Contraction:

The left atrium contraction assay was performed at Ricerca Biosciences, LLC (catalog no 407500 Adrenergic beta1), using left atria from Dunkin Hartley Guinea pig with body weight of 600+/−80 g (Arch. Int. Pharmacodyn. 1971: 191:133-141.).

Sino-Atrial Node Beating Rate:

New Zealand white female rabbits were killed by exsanguination after a deep anesthesia using a mixture of ketamine/xylazine, i.v. The heart was quickly removed and placed in Tyrode's solution. This solution was continuously gassed with 95% $O_2$, 5% $CO_2$, and previously warmed to approximately 36±0.5° C. The right atrium was separated from the rest of the heart. The preparations were mounted in a tissue bath and kept at 37±0.5° C. for at least one hour stabilization. Action potentials (AP) were intracellularly recorded with a standard glass microelectrode filled with 3 M KCl, connected to a high input impedance-neutralizing amplifier (VF-180 microelectrode amplifier, Bio-Logic). The AP were displayed on a digital oscilloscope (HM-407 oscilloscope, HAMEG), analyzed by means of high resolution data acquisition system (Notocord software hem 4.2, Notocord SA, Croissy, France). After one hour of stabilization, compounds were added to the Tyrode's solution at the increasing concentrations, each concentration being maintained for 30 minutes. There was no wash-out between two concentrations. Electrophysiological measurements were made by analyzing action potentials during the experimental protocol at the end of the 30 minute perfusion period. The SA spontaneous frequency was evaluated by counting the number of beats every 10 seconds to express the results in number of beats per minute (bpm). Data were expressed as mean±SEM.

Automaticity:

Automaticity was investigated in the isolated Langendorff perfused rabbit hearts, conducted by Hondeghem Pharmaceuticals Consulting N.V., B-8400 Oostende, Belgium. The tests were run in on hearts from albino female rabbits weighing about 2.5 kg and having an age of approximately 3 months. The compound effects were measured in a fully automated model using isolated rabbit heart perfused according to the Langendorff technique. The spontaneously beating heart is retrogradely perfused with increasing concentrations of the test item. One electrode is carefully placed on the left atrium in order to record the cycle length of the sinus node automaticity.

Figure 2A:
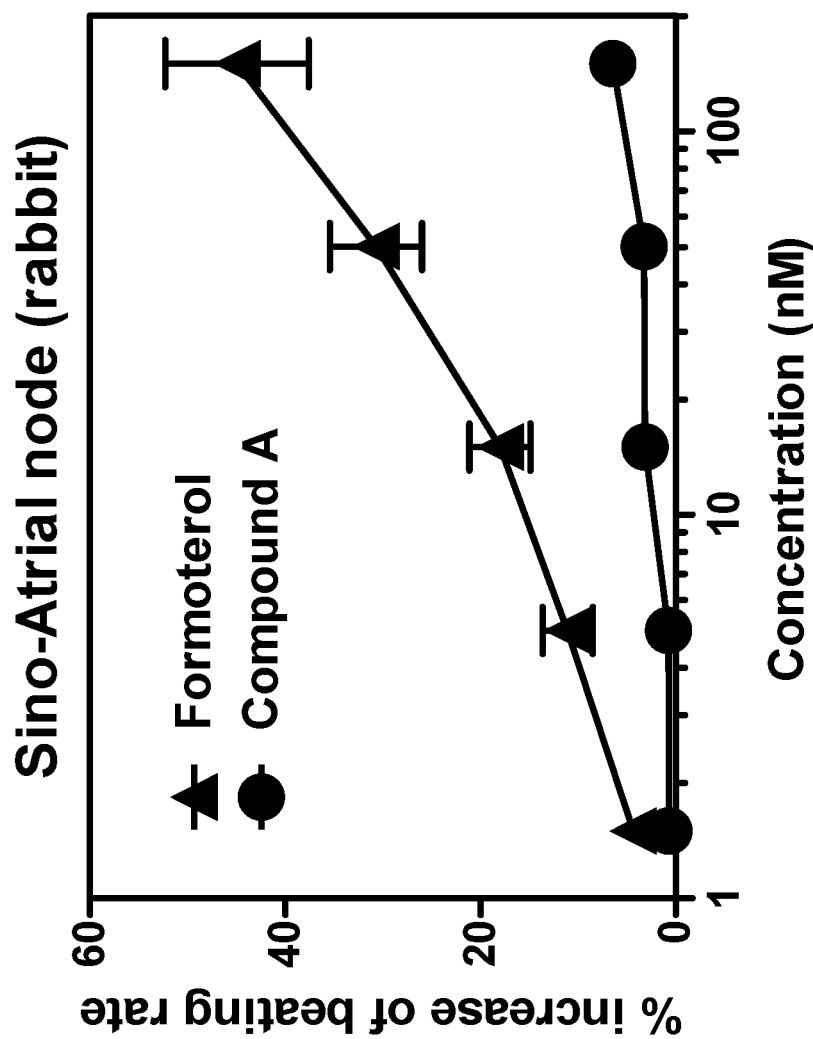
FIG. 2a shows the increase of beating rate in isolated rabbit sino-atrial nodes when using formoterol vs compound A (compound of the invention).
Figure 2B:
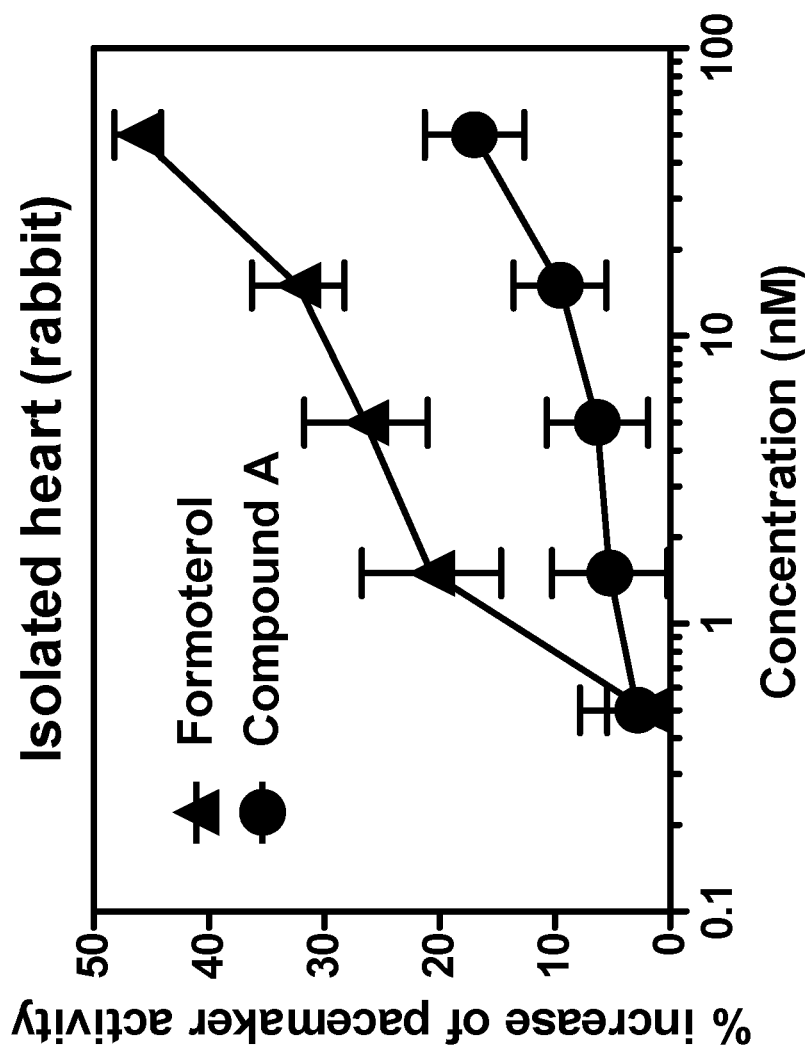
FIG. 2b shows the increase of pacemaker activity in isolated rabbit hearts when using formoterol vs compound A (compound of the invention).

FIGS. 2a and 2b show the results obtained when comparing formoterol with compound of the invention (compound A).

Compound A shows no effects on left atrium contraction up to 10 μM and less direct effects on the pacemaker activity, compared to Formoterol.

| | Formoterol | Compound A |
|---|---|---|
| Left atrium contraction $EC_{50}$ (n = 2) | 17 nM | >10 μM |
| Sino-Atrial node beating rate, maximum increase (n = 6) | +45% | +6.2% |
| Automaticity, maximum increase (n = 3) | +46% | +17% |

Values in FIGS. 2a and 2b are expressed as means ± SEM; Sino-atrial node (n = 6), isolated heart (n = 3)

Example 9

Effects of Formoterol and Compound A on the Heart Rate In Vivo

Wistar Han (W-H) IGS (International Genetic Standard) rats (Crl:WI(Han)) were purchased from Charles River Laboratories. Femoral arterial and venous catheters were chronically implanted and exteriorized through a spring tether-swivel system and housed in specialized cages. Arterial catheter was connected to a pressure transducer to continuously measure pulse pressure, mean arterial pressure and heart rate, which was derived from the blood pressure signal, via a digital data acquisition system. Compounds were administered via s.c catheter implanted through the skin buttun. Values are expressed as means±SEM (n=3).

Figure 3A:
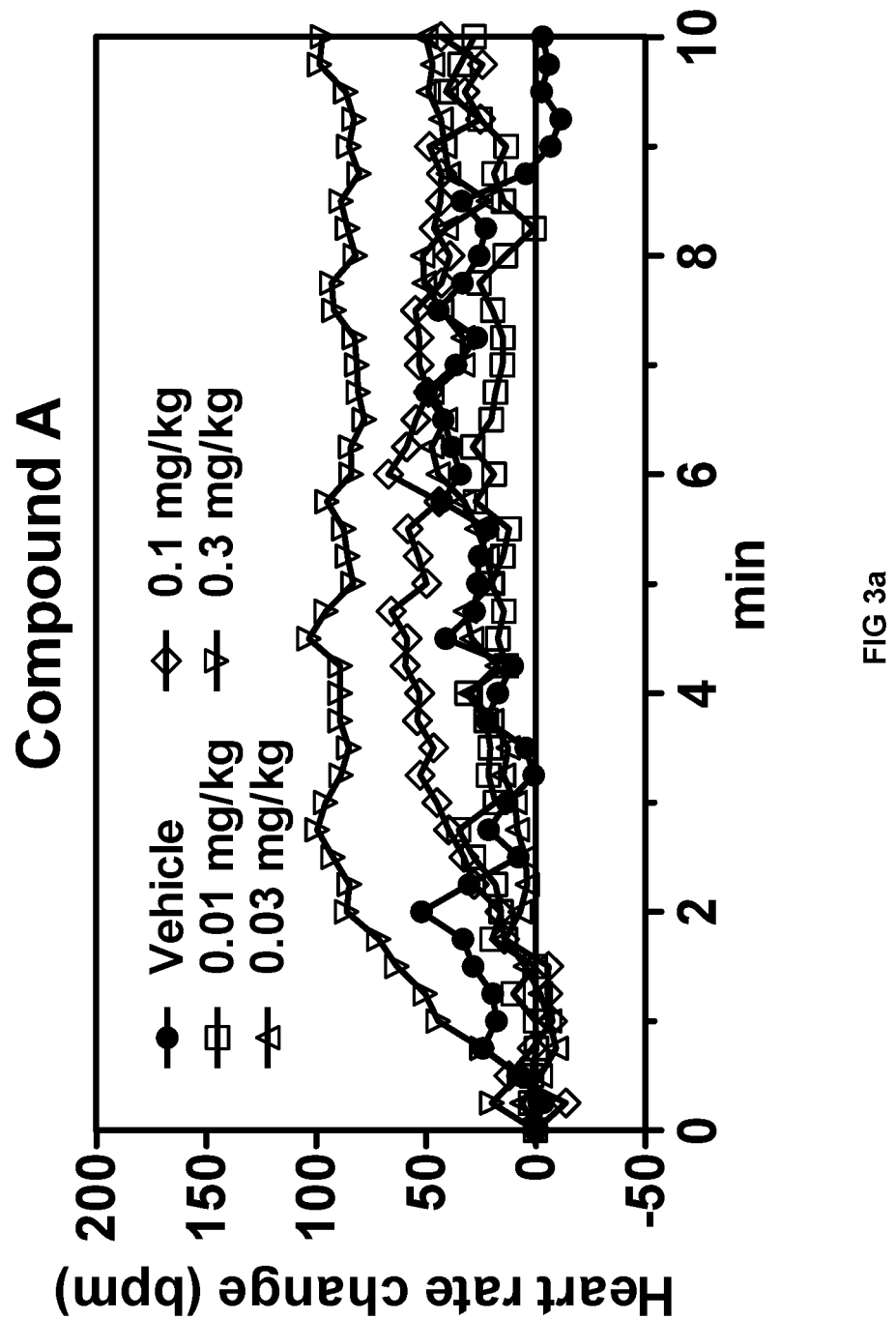
FIGS. 3a and 3b show the heart rate change in rats upon a s.c. bolus injection of Compound A (compound of the invention) or formoterol respectively.
Figure 3B:
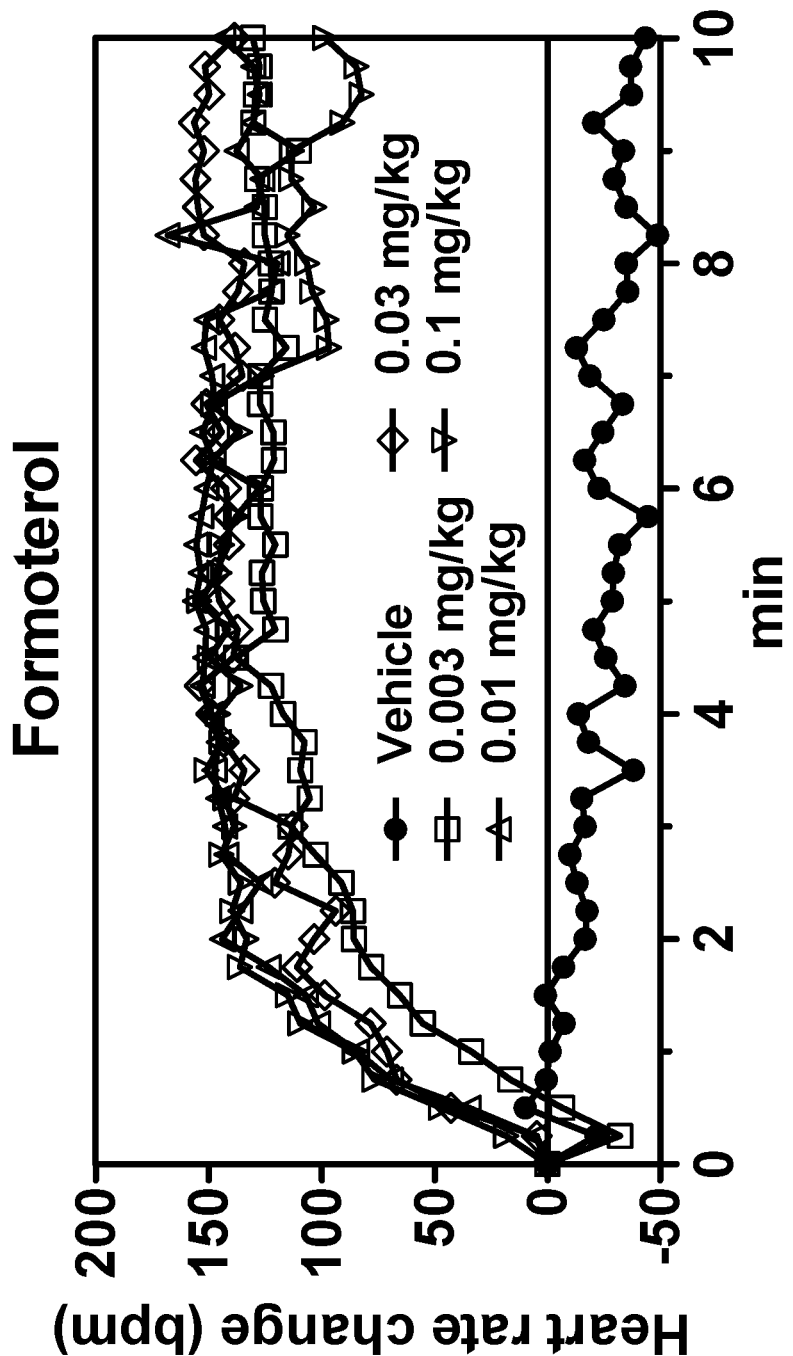
Figure 3C:
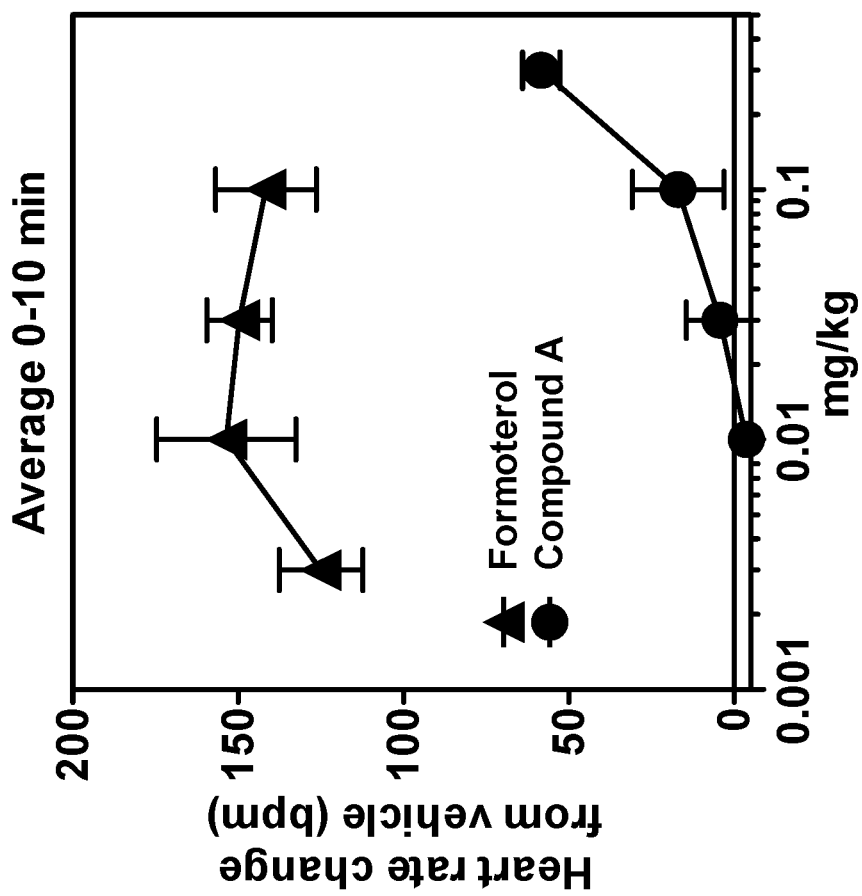
FIG. 3c compares the average heart rate change in rats when administering formoterol vs compound A (compound of the invention).

Compound A shows less heart rate increases compared to formoterol when administered with s.c. bolus, up to 0.3 mg/kg as shown in FIGS. 3a, 3b and 3c.

Example 10

Effects of Formoterol and Compound A on the Heart Rate In Vivo

Rhesus monkeys, 24 females with body weight around 4 to 8 kg, were randomized into 4 groups of n=6. The animals were restrained on a chair up to 4 hours after single subcutaneous administration of compounds, and then returned to their pens. Heart rates were measured using a Surgivet V3304 device. Values are expressed as means±SEM (n=6).

Figure 4A:
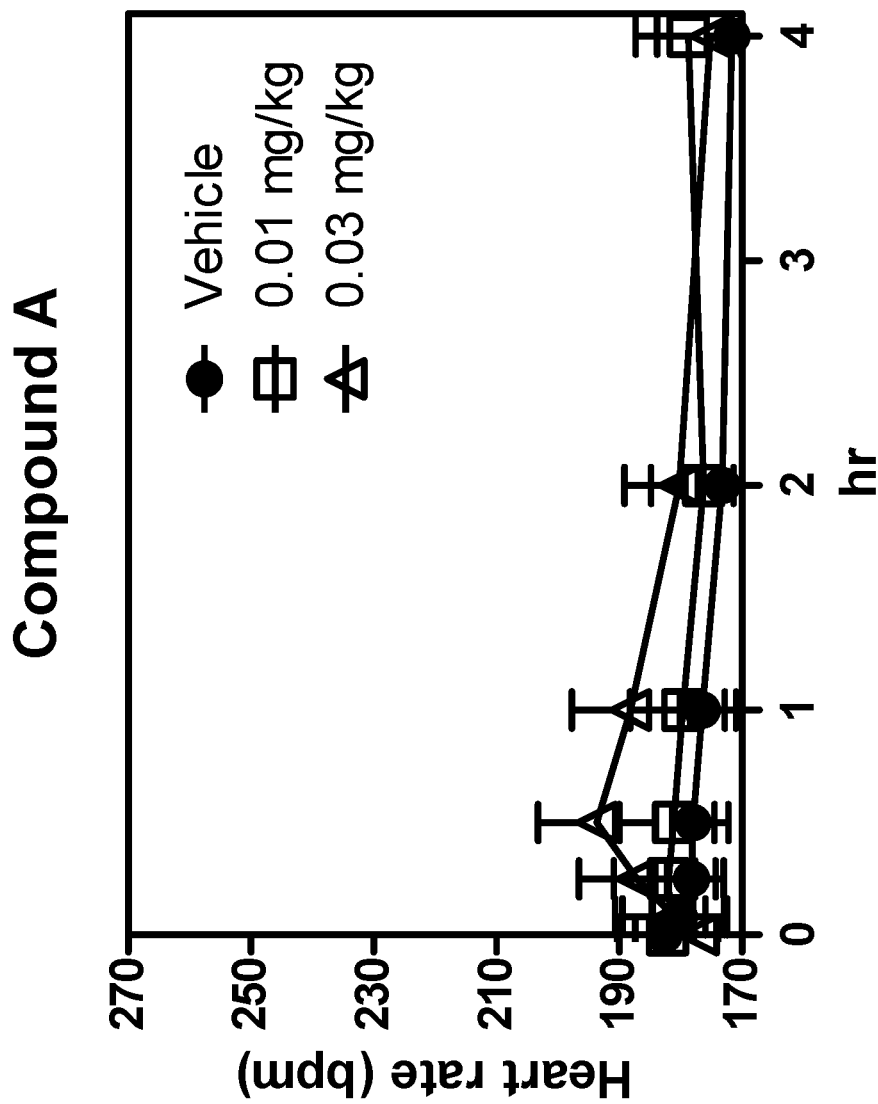
FIGS. 4a and 4b show the heart rate change in rhesus monkeys upon a s.c. bolus injection of Compound A (compound of the invention) or formoterol respectively.
Figure 4B:
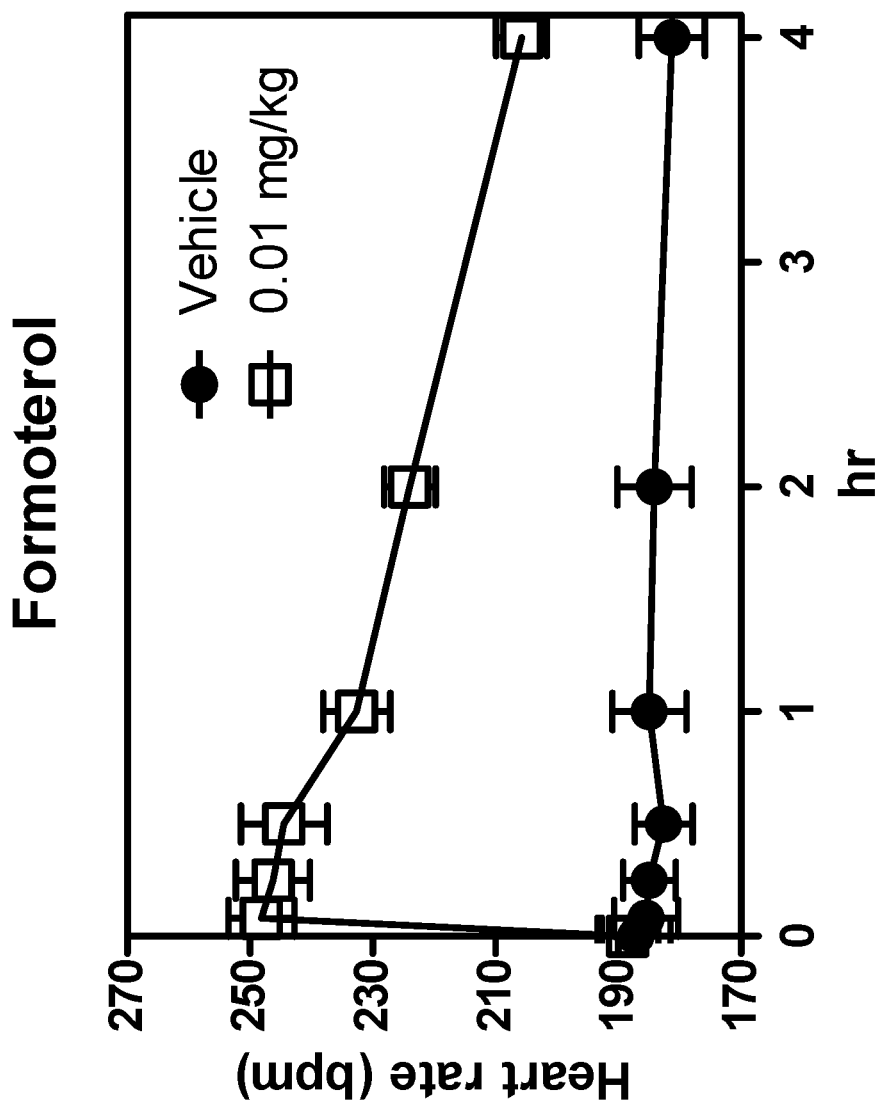

Compound A shows less heart rate increase compared to formoterol when administered as a s.c. bolus, up to 0.03 mg/kg as shown in FIGS. 4a and 4b.

Example 11

Effect of Compound A, its Enantiomer (Compound B) and its Racemate Compound A/B) on Serotonin 5-$HT_{2C}$ Receptor Human recombinant hr5-$HT_{2C}$ CHO cell membranes (Biosignal Packard, USA) and $^3$H-Mesulergine (NEN Life Science Products, USA, 1 nM) are used for measuring the binding affinity of the compounds to human 5-$HT_{2C}$ receptor. Non-specific binding is evaluated in the presence of 1 µM Mesulergine. Fifty µL each of membrane, ligand and compound in a total volume of 250 µL are incubated in 96-well plates for 60 min at 22° C. in a buffer containing 50 mM Tris, 0.1% ascorbic acid, 10 µM Pargyline, pH 7.7. The plates are filtrated, washed 3 times in ice-cold 50 mM Tris, dried and measured in Topcount.

CHO-K1 cells coexpressing mitochondrial apoaequorin, recombinant Serotonin 5-$HT_{2Cne}$ and the promiscuous G protein $G_{\alpha 16}$, grown to mid-log phase in culture media without antibiotics were detached with PBS-EDTA, centrifuged and resuspended in assay buffer (DMEM/HAM's F12 with HEPES, without phenol red+0.1% BSA protease free) at a concentration of 1×10$^6$ cells/ml. Cells were incubated at room temperature for at least 4 h with coelenterazine h. Reference agonist was a-methyl-5-HT. For agonist testing, 50 µL of cell suspension were mixed with 50 µL of test or reference agonist in a 96-well plate. The resulting emission of light is recorded using Hamamatsu Functional Drug Screening System 6000 (FDSS 6000) luminometer. Agonist activity of test compound was expressed as a percentage of the activity of the reference agonist at its $EC_{100}$ concentration.

| Serotonin 5-$HT_{2C}$ | Binding | CHO $EC_{50}$ ($E_{max}$ %) |
|---|---|---|
| 5-HT | n.d. | 0.24 nM |
| Compound A (R) | 11 µM | 280 nM (83%) |
| Compound B (S) | 0.8 µM | 19.7 nM (99%) |
| Compound A/B | 1.7 µM | 25 nM (113%) |

Compound A is 50-fold less active on 5-$HT_{2C}$ when compared to β2 AR agonist activity (5.6 nM), while its enantiomer Compound B is very weak on β2 AR with $EC_{50}$ of 950 nM but much more potent on 5-$HT_{2C}$ with $EC_{50}$ of 19.7 nM, showing inversed selectivity on the target.

Compound A is also over 10-fold less active on 5-$HT_{2C}$ when compared to the racemate or the (S) enantiomer, suggesting that the side-effect profile of this compound is advantageous.

Example 12

Hard Capsules

TABLE 1

Composition of (R)-7-(2-(1-(4-butoxyphenyl)-2-methylpropan-2-ylamino)-1-hydroxyethyl)-5-hydroxybenzo[d]thiazol-2(3H)-one hard capsules

| Ingredient for capsule fill | % (w/w) for 0.5 mg capsules | % (w/w) for 5 mg capsules | % (w/w) for 10 mg capsules |
|---|---|---|---|
| (R)-7-(2-(1-(4-butoxyphenyl)-2-methylpropan-2-ylamino)-1-hydroxyethyl)-5-hydroxybenzo[d]thiazol-2(3H)-one acetate salt | 0.60 | 5.95 | 11.90 |
| Avicel PH101 | 71.90 | 66.55 | 60.60 |
| Lactose Spray Dried | 20.00 | 20.00 | 20.00 |
| Ac-di-Sol | 6.00 | 6.00 | 6.00 |
| Aerosil 200 | 0.50 | 0.50 | 0.50 |
| Magnesium stearate | 1.00 | 1.00 | 1.00 |

Hard gelatin capsules, each comprising as active ingredient 0.5, 5 or 10 mg of the (R)-7-(2-(1-(4-butoxyphenyl)-2-methylpropan-2-ylamino)-1-hydroxyethyl)-5-hydroxybenzo[d]thiazol-2(3H)-one (equivalent to 0.60, 5.95 and 11.90 mg respectively of (R)-7-(2-(1-(4-butoxyphenyl)-2-methylpropan-2-ylamino)-1-hydroxyethyl)-5-hydroxybenzo[d]thiazol-2(3H)-one acetate salt) with the composition listed in Table 1 can be prepared as follows:

Preparation of Pre-Mix:

(R)-7-(2-(1-(4-butoxyphenyl)-2-methylpropan-2-ylamino)-1-hydroxyethyl)-5-hydroxybenzo[d]thiazol-2(3H)-one acetate salt with a portion of Avicel PH101 and Aerosil 200 were passed through a suitable sieve and mixed in a tumble blender (approximately 100-300 rotations).

Preparation of Final Blend:

The above pre-mix and the remaining quantity of Avicel PH101, Lactose Spray Dried, and Ac-di-Sol were passed through a suitable sieve and mixed in a tumble blender (approximately 100-300 rotations).

This mixture was then passed through a sieve of approximately 0.5-1.0 mm mesh-size and mixed again (approximately 100-300 rotations).

Similarly, the required amount of sieved magnesium stearate was added to the bulk powder and then mixed in the same blending container at approximately 30-150 rotations.

Filling:

This final blend is encapsulated into capsules using automated equipment. The weight ratio of capsule fill to empty capsule shells is 2:1.

Example 13

Hard Capsules

TABLE 2

Composition of (R)-7-(2-(1-(4-butoxyphenyl)-2-methylpropan-2-ylamino)-1-hydroxyethyl)-5-hydroxybenzo[d]thiazol-2(3H)-one hard capsules

| Ingredient for capsule fill | % (w/w) for 0.5 mg capsules | % (w/w) for 5 mg capsules | % (w/w) for 10 mg capsules |
|---|---|---|---|
| (R)-7-(2-(1-(4-butoxyphenyl)-2-methylpropan-2-ylamino)-1-hydroxyethyl)-5-hydroxybenzo[d]thiazol-2(3H)-one acetate salt | 0.60 | 5.95 | 11.90 |
| CA-HYD-Phosphate | 71.90 | 66.55 | 60.60 |
| Avicel PH101 | 20.00 | 20.00 | 20.00 |
| Sodium Carboxymethyl Starch | 6.00 | 6.00 | 6.00 |
| Aerosil 200 | 0.50 | 0.50 | 0.50 |
| Magnesium stearate | 1.00 | 1.00 | 1.00 |

The capsules with composition shown in Table 2 can be prepared following the process described in Example 12.

Example 14

Hard Capsules

TABLE 3

Composition of (R)-7-(2-(1-(4-butoxyphenyl)-2-methylpropan-2-ylamino)-1-hydroxyethyl)-5-hydroxybenzo[d]thiazol-2(3H)-one hard gelatin capsules

| Ingredient for capsule fill | % (w/w) for 0.5 mg capsules | % (w/w) for 5 mg capsules | % (w/w) for 10 mg capsules |
|---|---|---|---|
| (R)-7-(2-(1-(4-butoxyphenyl)-2-methylpropan-2-ylamino)-1-hydroxyethyl)-5-hydroxybenzo[d]thiazol-2(3H)-one acetate salt | 0.60 | 5.95 | 11.90 |
| Mannitol DC | 64.40 | 59.05 | 53.10 |
| STA-RX 1500 | 23.00 | 23.00 | 23.00 |
| Low substitute hydroxypropyl cellulose | 10.00 | 10.00 | 10.00 |
| Talc | 1.00 | 1.00 | 1.00 |
| Magnesium stearate | 1.00 | 1.00 | 1.00 |

The capsules with composition shown in Table 3 can be prepared following the process described in Example 12.

Example 15

Tablets

The formulations listed in Example 14 (Table 3) can also be converted into tablets with dosage strengths of 0.5 mg, 5 mg and 10 mg, by following the process described below.

Preparation of Pre-Mix:

(R)-7-(2-(1-(4-butoxyphenyl)-2-methylpropan-2-ylamino)-1-hydroxyethyl)-5-hydroxybenzo[d]thiazol-2(3H)-one acetate salt with a portion of Mannitol DC and the Talc are passed through a suitable sieve and mix in a tumble blender (approximately 100-300 rotations).

Preparation of Final Blend:

The above pre-mix and the remaining quantity of Mannitol DC, STA-RX 1500, and low substitute hydroxypropyl cellulose are passed through a suitable sieve and mixed in a tumble blender (approximately 100-300 rotations). This mixture is then sieved through a sieve of approximately 0.5-1.0 mm mesh-size and mixed again (approximately. 100-300 rotations). Finally, the magnesium stearate sieved through a handsieve at approximately 0.5-1.0 mm mesh-size is mixed to the previous blend in a tumble blender (approximately 30-150 rotations).

Compression:

The above final blend is compressed to a tablet-core of approximately 100 mg, using the dosage specific tooling (e.g. approximately 6 mm, round, curved).

Example 16

Tablets

TABLE 4

Composition of (R)-7-(2-(1-(4-butoxyphenyl)-2-methylpropan-2-ylamino)-1-hydroxyethyl)-5-hydroxybenzo[d]thiazol-2(3H)-one tablets

| Ingredient for Tablet cores | % (w/w) for 0.5 mg tablets | % (w/w) for 5 mg tablets | % (w/w) for 10 mg tablets |
|---|---|---|---|
| (R)-7-(2-(1-(4-butoxyphenyl)-2-methylpropan-2-ylamino)-1-hydroxyethyl)-5-hydroxybenzo[d]thiazol-2(3H)-one acetate salt | 0.60 | 5.95 | 11.90 |
| Avicel PH101 | 65.40 | 60.05 | 54.10 |
| Lactose Spray Dried | 20.00 | 20.00 | 20.00 |
| HP-Cellulose 100 | 4.00 | 4.00 | 4.00 |
| Ac-di-Sol | 8.00 | 8.00 | 8.00 |
| Aerosil 200 | 1.00 | 1.00 | 1.00 |
| Magnesium stearate | 1.00 | 1.00 | 1.00 |

Tablets, each comprising as active ingredient 0.5, 5 or 10 mg of the (R)-7-(2-(1-(4-butoxyphenyl)-2-methylpropan-2-ylamino)-1-hydroxyethyl)-5-hydroxybenzo[d]thiazol-2(3H)-one (equivalent to 0.60, 5.95 and 11.90 mg respectively of (R)-7-(2-(1-(4-butoxyphenyl)-2-methylpropan-2-ylamino)-1-hydroxyethyl)-5-hydroxybenzo[d]thiazol-2(3H)-one acetate salt) with the composition listed in Table 4 can be prepared as follows:

Preparation of Pre-Mix:

(R)-7-(2-(1-(4-butoxyphenyl)-2-methylpropan-2-ylamino)-1-hydroxyethyl)-5-hydroxybenzo[d]thiazol-2(3H)-one acetate salt with a portion of Lactose Spray Dried and Aerosil 200 (e.g. approximately 0.5%) are passed through a suitable sieve and mixed in a tumble blender (approximately 100-300 rotations).

The above pre-mix and the remaining quantity of Lactose Spray Dried, Avicel PH101, HP-Cellulose 100 and Ac-di-Sol (e.g. approximately 4.0%) are passed through a suitable sieve and mixed in a tumble blender (approximately 100-300 rotations).

Pass this mixture through a sieve of approximately 0.5-1.0 mm mesh-size and mix again (approximately 100-300 rotations).

Similarly, the required amount of sieved magnesium stearate (e.g. approximately 0.5%) is added to the bulk powder and then mixed in the same blending drum (approximately 30-150 rotations).

Roller Compaction:

The above blend is roller compacted using a compactor equipment. The compacted material is milled through a sieve of approximately 0.5-1.0 mm mesh size using a milling equipment.

Preparation of Final Blend:

The above pre-mix and the quantity of Ac-di-Sol (e.g. approximately 4.0%) and Aerosil 200 (e.g. approximately 0.5%) are passed through a suitable sieve with mix in a tumble blender (approximately 100-300 rotations).

The remaining magnesium stearate sieved through a handsieve at approximately 0.5-1.0 mm mesh-size is mixed to the final blend in a tumble blender (approximately 30-150 rotations).

Compression:

The above final blend is compressed on a rotary press to cores of appropriate weight (e.g. 100 mg), using the dosage specific tooling (e.g. approximately 6 mm, round, curved).

Example 17

Tablets

TABLE 5

Composition of (R)-7-(2-(1-(4-butoxyphenyl)-
2-methylpropan-2-ylamino)-1-hydroxyethyl)-5-
hydroxybenzo[d]thiazol-2(3H)-one Tablets

| Ingredient for capsule fill | % (w/w) for 0.5 mg tablets | % (w/w) for 5 mg tablets | % (w/w) for 10 mg tablets |
| --- | --- | --- | --- |
| (R)-7-(2-(1-(4-butoxyphenyl)-2-methylpropan-2-ylamino)-1-hydroxyethyl)-5-hydroxybenzo[d]thiazol-2(3H)-one acetate salt | 0.60 | 5.95 | 11.90 |
| Mannitol DC | 58.40 | 53.05 | 47.10 |
| STA-RX 1500 | 23.00 | 23.00 | 23.00 |
| HP-Cellulose Low Subst | 10.00 | 10.00 | 10.00 |
| Kollidon VA64 | 6.00 | 6.00 | 6.00 |
| Talc | 1.00 | 1.00 | 1.00 |
| Magnesium stearate | 1.00 | 1.00 | 1.00 |

Preparation Process:
Preparation of Pre-Mix:

(R)-7-(2-(1-(4-butoxyphenyl)-2-methylpropan-2-ylamino)-1-hydroxyethyl)-5-hydroxybenzo[d]thiazol-2(3H)-one acetate salt with a portion of Mannitol DC and Talc (e.g. approximately 0.5%) are passed through a suitable sieve and mixed in a tumble blender (approximately 100-300 rotations).

The above pre-mix and the remaining quantity of Mannitol DC, STA-RX 1500, Kollidon VA64, and a portion of HP-Cellulose Low Substituted (e.g. approximately 5.0%) are passed through a suitable sieve and mixed in a tumble blender (approximately 100-300 rotations).

Pass this mixture through a sieve of approximately 0.5-1.0 mm mesh-size and mix again (approximately 100-300 rotations).

Similarly, the required amount of sieved magnesium stearate (e.g. approximately 0.5%) is added to the bulk powder and then mixed in the same blending drum (approximately 30-150 rotations).

Roller Compaction:

The above blend is roller compacted using a compactor equipment. The compacted material is milled through a sieve of approximately 0.5-1.0 mm mesh size using a milling equipment.

Preparation of Final Blend:

The above pre-mix and the remaining quantity of low substituted hydroxypropyl cellulose (e.g. approximately 5.0%) and talc (e.g. approximately 0.5%) are passed through a suitable sieve with mix in a tumble blender (approximately 100-300 rotations).

The remaining magnesium stearate sieved through a handsieve at approximately 0.5-1.0 mm mesh-size is mixed to the final blend in a tumble blender (approximately 30-150 rotations).

Compression:

The above final blend is compressed on a rotary press to cores of appropriate weight (e.g. 100 mg), using the dosage specific tooling (e.g. approximately 6 mm, round, curved).

The invention claimed is:

1. A pharmaceutical composition in solid oral dosage form comprising 0.01 to 15% (w/w) of (R)-7-(2-(1-(4-butoxyphenyl)-2-methylpropan-2-ylamino)-1-hydroxyethyl)-5-hydroxybenzo[d]thiazol-2(3H)-one and one or more pharmaceutically acceptable excipients, wherein (R)-7-(2-(1-(4-butoxyphenyl)-2-methylpropan-2-ylamino)-1-hydroxyethyl)-5-hydroxybenzo[d]thiazol-2(3H)-one is in acetate salt form.

2. A pharmaceutical composition according to claim 1, comprising 0.01 to 5% (w/w) of (R)-7-(2-(1-(4-butoxyphenyl)-2-methylpropan-2-ylamino)-1-hydroxyethyl)-5-hydroxybenzo[d]thiazol-2(3H)-one.

3. A pharmaceutical composition according to claim 1, comprising 0.1 to 1% (w/w) of (R)-7-(2-(1-(4-butoxyphenyl)-2-methylpropan-2-ylamino)-1-hydroxyethyl)-5-hydroxybenzo[d]thiazol-2(3H)-one.

4. A pharmaceutical composition according to claim 1 which is a tablet or a capsule.

5. Pharmaceutical composition according to claim 1, wherein the one or more excipients is selected from filler, lubricant, glidant, disintegrant and binder.

6. Pharmaceutical composition according to claim 5, wherein the filler is present in an amount of 15-90% (w/w).

7. Pharmaceutical composition according to claim 5, wherein a lubricant is present in an amount of 0.1-1% (w/w).

8. Pharmaceutical composition according to claim 5, wherein a glidant is present in an amount of 0.1-1% (w/w).

9. Pharmaceutical composition according to claim 5, wherein a binder is present in an amount of 1-20% (w/w).

10. Pharmaceutical composition according to claim 5, wherein a disintegrant is present in an amount of 1-20% (w/w).

11. A method for the manufacture of a pharmaceutical composition suitable for oral administration comprising (R)-7-(2-(1-(4-butoxyphenyl)-2-methylpropan-2-ylamino)-1-hydroxyethyl)-5-hydroxybenzo[d]thiazol-2(3H)-one comprising the steps of
 a) mixing (R)-7-(2-(1-(4-butoxyphenyl)-2-methylpropan-2-ylamino)-1-hydroxyethyl)-5-hydroxybenzo[d]thiazol-2(3H)-one acetate salt with a filler and a glidant to form a pre-mix;
 b) mixing the pre-mix obtained in step a) with a further filler and a disintegrant to obtain a powder;
 c) adding a lubricant to the powder obtained in step b) to obtain a final blend; and
 d) processing the final blend obtained in step c) into a pharmaceutical composition suitable for oral administration.

12. A method according to claim 11, wherein (R)-7-(2-(1-(4-butoxyphenyl)-2-methylpropan-2-ylamino)-1-hydroxyethyl)-5-hydroxybenzo[d]thiazol-2(3H)-one acetate salt is used in an amount sufficient to provide 0.01-15%

(w/w) (R)-7-(2-(1-(4-butoxyphenyl)-2-methylpropan-2-ylamino)-1-hydroxyethyl)-5-hydroxybenzo[d]thiazol-2(3H)-one in the pharmaceutical composition.

13. A method of treatment of muscular dystrophy, disuse-related atrophy, cachexia or sarcopenia comprising administering orally a pharmaceutical composition claim 1 to a subject in need thereof.

* * * * *